(12) United States Patent
Tang et al.

(10) Patent No.: US 8,178,575 B2
(45) Date of Patent: May 15, 2012

(54) DERIVATIVES OF AZABICYCLO OCTANE, THE METHOD OF MAKING THEM AND THE USES THEREOF AS INHIBITORS OF DIPEPTIDYL PEPTIDASE IV

(75) Inventors: Pengcho Tang, Shanghai (CN); Zhigang Lin, Shanghai (CN); Hejun Lü, Shanghai (CN); Fuqiang Zhao, Shanghai (CN); Li Li, Shanghai (CN)

(73) Assignees: Shanghai Hengrui Pharmaceutical Co., Ltd., Shanghai (CN); Jiangsu Hansoh Pharmaceutical Co., Ltd., Jiangsu (CN)

( * ) Notice: Subject to any disclaimer, the term of this patent is extended or adjusted under 35 U.S.C. 154(b) by 288 days.

(21) Appl. No.: 12/518,259

(22) PCT Filed: Oct. 30, 2007

(86) PCT No.: PCT/CN2007/070990
§ 371 (c)(1),
(2), (4) Date: Jun. 8, 2009

(87) PCT Pub. No.: WO2008/089636
PCT Pub. Date: Jul. 31, 2008

(65) Prior Publication Data
US 2010/0016314 A1    Jan. 21, 2010

(30) Foreign Application Priority Data
Jan. 23, 2007    (CN) .......................... 2007 1 0004330

(51) Int. Cl.
*A61K 31/40* (2006.01)
*C07D 209/00* (2006.01)
(52) U.S. Cl. ...................... 514/414; 548/452
(58) Field of Classification Search ................. 514/414; 548/452
See application file for complete search history.

(56) References Cited

U.S. PATENT DOCUMENTS

| | | | |
|---|---|---|---|
| 5,736,550 A | 4/1998 | Kikuchi et al. | |
| 6,110,949 A | 8/2000 | Villhauer | |
| 6,395,767 B2 * | 5/2002 | Robl et al. ................... 514/412 |
| 2005/0130981 A1 | 6/2005 | Aranyl et al. | |
| 2009/0176847 A1 | 7/2009 | Tang et al. | |

FOREIGN PATENT DOCUMENTS

| | | |
|---|---|---|
| CN | 1639159 A | 7/2005 |
| CN | 1798559 A | 7/2006 |
| CN | 101050194 A | 10/2007 |
| WO | WO-98/19998 A2 | 5/1998 |
| WO | WO-2006/028961 A2 | 3/2006 |

OTHER PUBLICATIONS

Fairhurst et al. CAS: 141:350042, 2004.*
Hansen, L., et al., "Glucagon-Like Peptide-1-(7-36)Amide is Transformed to Glucagon-Like Peptide-1-(9-36)Amide by Dipeptidyl Peptidase IV in the Capillaries Supplying the L. Cells of the Porcine Intestine" The Endocrine Society, vol. 140 No. 11, 1999, pp. 5356-5363.
Xiao. J., et al. "Quantitative Structure-activity Relationship of Dipeptidyl Peptidase IV Inhibitors" Institute of Material Medica, Chinese Academy of Medical Sciences and Peking Union Medical College, Beijing, Acta Chimica Sinica, vol. 63, No. 8, 2005 pp. 757-763.
Mihovilovic D. M., et al., "Application of dry-state adsorption condition (DSAC) Pauson-Khan cyclization for the synthesis of perhydrocyclopenta[c]pyrroles" Issue in Honor of Prof. Fritz Sauter, Arkat, ARKIVOC, 2001, pp. 28-33.
Barluenga, J., et al., "Zirconium-Mediated Intramolecular Coupling of Terminal Alkynes and Their Subsequent Carbonylation: Novel Synthesis of Seven- and Eight-Membered Heterocycles", Chemical Eur. J. vol. 3, No. 8, 1997, pp. 1324-1336.
Becker, D. P. and D. L. Flynn, "Studies of the Solid-Phase Pauson-Khand Reaction: Selective in-situ Enone Reduction to 3-Azabicyclo[3.3.0] octanones" Tetrahedron Letters, vol. 34, No. 13, 1993, pp. 2087-2090.

* cited by examiner

*Primary Examiner* — Rei-tsang Shiao
(74) *Attorney, Agent, or Firm* — Birch, Stewart, Kolasch & Birch, LLP

(57) ABSTRACT

Derivatives of azabicyclo octane presented by formula (I), the method of making them, and the compositions containing the same and the uses thereof as inhibitors of dipeptidyl peptidase IV (DPP-IV), wherein the substitutes in formula (I) have the same meanings as what is mentioned in the descriptions.

10 Claims, No Drawings

DERIVATIVES OF AZABICYCLO OCTANE, THE METHOD OF MAKING THEM AND THE USES THEREOF AS INHIBITORS OF DIPEPTIDYL PEPTIDASE IV

FIELD OF THE INVENTION

This invention relates to derivatives of azabicyclo octane, the method of making them, and the compositions containing the same and the uses thereof, particularly their pharmaceutical use as inhibitors of dipeptidyl peptidase IV (DPP-IV).

BACKGROUND OF THE INVENTION

Diabetes refers to a disease process derived from multiple causative factors and characterized by elevated levels of plasma glucose or hyperglycemia along with sugar, fat and protein metabolism disorder caused by insulin secretion and/or the action defects. Diabetes is an ancient disease, and due to the human body absolute or relative lack of insulin resulting in increased concentrations of glucose in the blood which largely discharges in urine with more drink, more urine, more food, weight loss, dizziness, weakness and other symptoms.

Dipeptidyl peptidase-IV (DPPIV) is a serine protease which cleaves N-terminal dipeptides from a peptide chain containing, preferably, a proline residue in the penultimate position. Although the biological role of DPPIV in mammalian systems has not been completely established, it is believed to play an important role in neuropeptide metabolism, T-cell activation, attachment of cancer cells to the endothelium and the entry of HIV into lymphoid cells (WO98/19998).

More recently, it was discovered that DPPIV is responsible for inhibiting the secretion of glucagon-like peptide (GLP)-1. More particularly, DPPIV cleaves the amino-terminal His-Ala dipeptide of GLP-1, degrading active GLP-1(7-36)$NH_2$ into inactive GLP-1(9-36)$NH_2$ (Endocrinology, 1999, 140: 5356-5363). Under the physiological condition, the half-life of the whole GLP-1 in blood circulation is short, the inactive metabolite from GLP-1 degraded by DPPIV can combine with GLP-1 receptor to antagonize the active GLP-1, so the physiological response to GLP-1 is shortened. The endogenous even exogenous GLP-1 can be entirely protected by the DPPIV inhibitor from being deactivated by DPPIV, and the GLP-1 bioactivity can be significantly increased (5- to 10-fold). Since GLP-1 is a major stimulator of pancreatic insulin secretion and can directly effect on glucose disposal, the DPPIV inhibitor is well useful for treating non-insulin-dependent diabetes mellitus (NIDDM) (U.S. Pat. No. 6,110,949).

SUMMARY OF THE INVENTION

Accordingly, the present invention relates to compounds having formula (I) or pharmaceutically acceptable salts thereof:

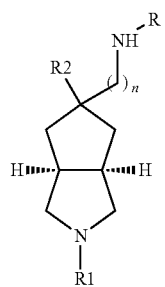

(I)

wherein:

R is selected from the group consisting of alkyl, cycloalkyl, haloalkyl, aryl, heteroaryl, aminocarbonyl alkyl, amide alkyl, aminocarbonyl alkyl having heterocycle and aminoalkyl, wherein the heterocycle is 5- or 6-membered hetero ring further substituted with one or more groups selected from the group consisting of alkyl, aryl, heteroaryl, haloalkyl, haloalkoxyl, hydroxyl, amino, alkylamino, amide group, aminocarbonyl, cyano, alkynyl, alkoxyl, aryloxyl, aminoalkyl, hydroxyalkyl, heterocyclo alkyl, carboxylic acid, carboxylic ester and halogen;

$R_1$ is selected from the group consisting of hydrogen, alkyl, cycloalkyl, heterocyclo alkyl, aryl, heteroaryl, —C(O)$NR_3R_4$, —C(O)$R_3$ and —C(O)$OR_3$, wherein the alkyl, cycloalkyl, heterocyclo alkyl, aryl or heteroaryl is further substituted with one or more groups selected from the group consisting of alkyl, aryl, hydroxyl, amino, alkoxyl, aryloxyl and heterocyclo alkyl;

$R_2$ is selected from the group consisting of hydrogen and methyl;

$R_3$ and $R_4$ are each independently selected from the group consisting of hydrogen, alkyl, cycloalkyl, aryl, heteroaryl and heterocyclo alkyl, wherein the alkyl, cycloalkyl, aryl, heteroaryl or heterocyclo alkyl is further substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, cyano, hydroxyalkyl, heterocyclo alkyl, heterocyclo alkoxyl, trifluoromethyl, carboxylic acid and carboxylic ester; and $R_3$ and $R_4$ are attached together with the N atom to form a 3 to 8 membered hetero ring, wherein the 3 to 8 membered hetero ring further contains one or more heteroatoms selected from the group consisting of N, O and S atom, and the 3 to 8 membered rings are further substituted with one or more groups selected from the group consisting of alkyl, aryl, heteroaryl, haloalkyl, haloalkoxyl, hydroxyl, amino, cyano, alkoxyl, aryloxyl, hydroxyalkyl, heterocyclo alkyl, carboxylic acid, carboxylic ester, halogen and —$NR_3R_4$; and n is an integer from 0 to 4.

Further, the present invention includes the compounds of formula (IA) or pharmaceutically acceptable salts thereof:

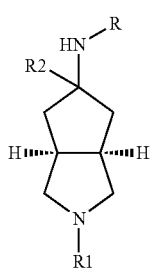

(IA)

wherein:

R is selected from the group consisting of alkyl, cycloalkyl, haloalkyl, aryl, heteroaryl, aminocarbonyl alkyl, amide alkyl, aminocarbonyl alkyl having heterocycle and aminoalkyl, wherein the heterocycle is 5- or 6-membered hetero ring further substituted with one or more groups selected from the group consisting of alkyl, aryl, heteroaryl, haloalkyl, haloalkoxyl, hydroxyl, amino, alkylamino, amide group, aminocarbonyl, cyano, allkynyl, alkoxyl, aryloxyl, aminoalkyl, hydroxyalkyl, heterocyclo alkyl, carboxylic acid, carboxylic ester and halogen;

R₁ is selected from the group consisting of hydrogen, alkyl, cycloalkyl, heterocyclo alkyl, aryl, heteroaryl, —C(O)NR₃R₄, —C(O)R₃ and —C(O)OR₃, wherein the alkyl, cycloalkyl, heterocyclo alkyl, aryl or heteroaryl is further substituted with one or more groups selected from the group consisting of alkyl, aryl, hydroxyl, amino, alkoxyl, aryloxyl and heterocyclo alkyl;

R₂ is selected from the group consisting of hydrogen and methyl;

R₃ and R₄ are each independently selected from the group consisting of hydrogen, alkyl, cycloalkyl, aryl, heteroaryl and heterocyclo alkyl, wherein the alkyl, cycloalkyl, aryl, heteroaryl or heterocyclo alkyl is further substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, cyano, hydroxyalkyl, heterocyclo alkyl, heterocyclo alkoxyl, trifluoromethyl, carboxylic acid and carboxylic ester; and R₃ and R₄ are attached together with the N atom to form a 3 to 8 membered hetero ring, wherein the 3 to 8 membered hetero ring further contains one or more heteroatoms selected from the group consisting of N, O and S atom, and the 3 to 8 membered rings are further substituted with one or more groups selected from the group consisting of alkyl, aryl, heteroaryl, haloalkyl, haloalkoxyl, hydroxyl, amino, cyano, alkoxyl, aryloxyl, hydroxyalkyl, heterocyclo alkyl, carboxylic acid, carboxylic ester, halogen and —NR₃R₄.

Preferably, in the compounds having formula (I) or pharmaceutically acceptable salts thereof, R is the following formula:

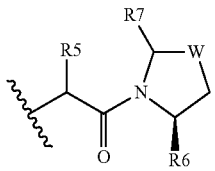

wherein R₅ is selected from the group consisting of hydrogen, alkyl, cycloalkyl, aryl, heteroaryl and heterocyclo alkyl, wherein the alkyl, cycloalkyl, aryl, heteroaryl or heterocyclo alkyl is further substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, alkylamino, cyano, hydroxyalkyl, heterocyclo alkyl, heterocyclo alkoxyl, carboxylic acid and carboxylic ester;

R₆ and R₇ are each independently selected from the group consisting of alkyl, aryl, heteroaryl, haloalkyl, haloalkoxyl, hydroxyl, amino, cyano, allkynyl, alkoxyl, aryloxyl, hydroxyalkyl, heterocyclo alkyl, carboxylic acid, carboxylic ester and halogen; and W is C, S or O atom.

Further, the present invention includes the compounds of formula (IB) or pharmaceutically acceptable salts thereof:

(IB)

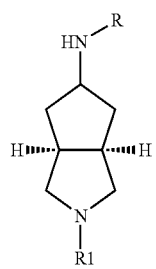

wherein R is the the following formula:

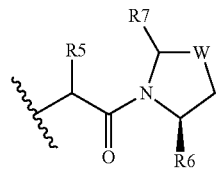

R₁ is selected from the group consisting of hydrogen, alkyl, cycloalkyl, heterocyclo alkyl, aryl, heteroaryl, —C(O)NR₃R₄, —C(O)R₃ and —C(O)OR₃, wherein the alkyl, cycloalkyl, heterocyclo alkyl, aryl or heteroaryl is further substituted with one or more groups selected from the group consisting of alkyl, aryl, hydroxyl, amino, alkoxyl, aryloxyl and heterocyclo alkyl;

R₃ and R₄ are each independently selected from the group consisting of hydrogen, alkyl, cycloalkyl, aryl, heteroaryl and heterocyclo alkyl, wherein the alkyl, cycloalkyl, aryl, heteroaryl or heterocyclo alkyl is further substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, cyano, hydroxyalkyl, heterocyclo alkyl, heterocyclo alkoxyl, trifluoromethyl, carboxylic acid and carboxylic ester; and R₃ and R₄ are attached together with the N atom to form a 3 to 8 membered hetero ring, wherein the 3 to 8 membered hetero ring further contains one or more heteroatoms selected from the group consisting of N, O and S atom, and the 3 to 8 membered rings are further substituted with one or more groups selected from the group consisting of alkyl, aryl, heteroaryl, haloalkyl, haloalkoxyl, hydroxyl, amino, cyano, alkoxyl, aryloxyl, hydroxyalkyl, heterocyclo alkyl, carboxylic acid, carboxylic ester, halogen and —NR₃R₄;

R₅ is selected from the group consisting of hydrogen, alkyl, cycloalkyl, aryl, heteroaryl and heterocyclo alkyl, wherein the alkyl, cycloalkyl, aryl, heteroaryl or heterocyclo alkyl is further substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, alkylamino, cyano, hydroxyalkyl, heterocyclo alkyl, heterocyclo alkoxyl, carboxylic acid and carboxylic ester;

R₆ and R₇ are each independently selected from the group consisting of alkyl, aryl, heteroaryl, haloalkyl, haloalkoxyl, hydroxyl, amino, cyano, alkynyl, alkoxyl, aryloxyl, hydroxyalkyl, heterocyclo alkyl, carboxylic acid, carboxylic ester and halogen; and W is C, S or O atom.

Further, the present invention includes the compounds of formula (IC) or pharmaceutically acceptable salts thereof:

(IC)

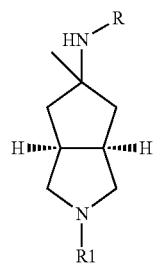

wherein R is the following formula:

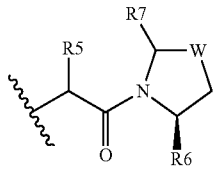

R₁ is selected from the group consisting of hydrogen, alkyl, cycloalkyl, heterocyclo alkyl, aryl, heteroaryl, —C(O)NR$_3$R$_4$, —C(O)R$_3$ and —C(O)OR$_3$, wherein the alkyl, cycloalkyl, heterocyclo alkyl, aryl or heteroaryl is further substituted with one or more groups selected from the group consisting of alkyl, aryl, hydroxyl, amino, alkoxyl, aryloxyl and heterocyclo alkyl;

R$_3$ and R$_4$ are each independently selected from the group consisting of hydrogen, alkyl, cycloalkyl, aryl, heteroaryl and heterocyclo alkyl, wherein the alkyl, cycloalkyl, aryl, heteroaryl or heterocyclo alkyl is further substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, cyano, hydroxyalkyl, heterocyclo alkyl, heterocyclo alkoxyl, trifluoromethyl, carboxylic acid and carboxylic ester; and R$_3$ and R$_4$ are attached together with the N atom to form a 3 to 8 membered hetero ring, wherein the 3 to 8 membered hetero ring further contains one or more heteroatoms selected from the group consisting of N, O and S atom, and the 3 to 8 membered rings are further substituted with one or more groups selected from the group consisting of alkyl, aryl, heteroaryl, haloalkyl, haloalkoxyl, hydroxyl, amino, cyano, alkoxyl, aryloxyl, hydroxyalkyl, heterocyclo alkyl, carboxylic acid, carboxylic ester, halogen and —NR$_3$R$_4$;

R$_5$ is selected from the group consisting of hydrogen, alkyl, cycloalkyl, aryl, heteroaryl and heterocyclo alkyl, wherein the alkyl, cycloalkyl, aryl, heteroaryl or heterocyclo alkyl is further substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, alkylamino, cyano, hydroxyalkyl, heterocyclo alkyl, heterocyclo alkoxyl, carboxylic acid and carboxylic ester;

R$_6$ and R$_7$ are each independently selected from the group consisting of alkyl, aryl, heteroaryl, haloalkyl, haloalkoxyl, hydroxyl, amino, cyano, alkynyl, alkoxyl, aryloxyl, hydroxyalkyl, heterocyclo alkyl, carboxylic acid, carboxylic ester and halogen; and W is C, S or O atom.

This invention provides compounds having formula (I) or pharmaceutically acceptable salts, wherein the salts comprise the salts formed with the acids selected from the group consisting of hydrochloric acid, p-toluenesulfonic acid, tartaric acid, maleic acid, lactic acid, methanesulfonic acid, sulfuric acid, phosphoric acid, citric acid, acetic acid and trifluoroacetic acid, preferably, the acids are p-toluenesulfonic acid, hydrochloric acid or trifluoroacetic acid.

In a particularly preferred embodiment, the compounds having formula (I) or pharmaceutically acceptable salts include:

| Example No. | Structure | Name |
|---|---|---|
| 1 | 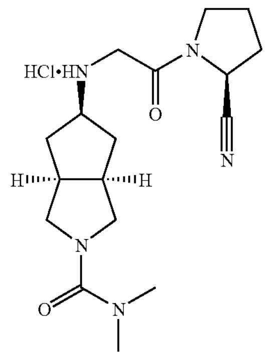 | cis-5-[2-(2-Cyano-pyrrolidin-1-yl)-2-oxo-ethylamino]-hexahydro-cyclopenta[c]pyrrole-2-carboxylic acid dimethylamide hydrochloride |
| 2 | 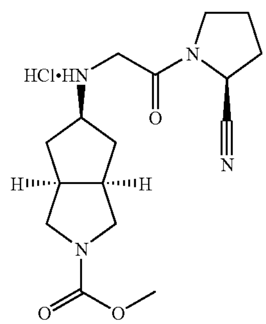 | cis-5-[2-(2-Cyano-pyrrolidin-1-yl)-2-oxoethylamino]-hexahydro-cyclopenta[c]pyrrole-2-carboxylic acid methyl ester hydrochloride |
| 3 | 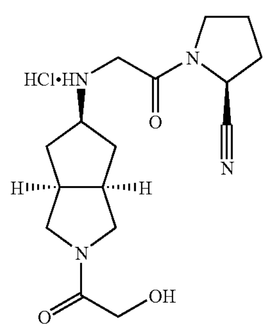 | cis-1-{2-[2-(2-Hydroxy-acetyl)-octahydro-cyclopenta[c]pyrrol-5-ylamino]-acetyl}-pyrrolidine-2-carbonitrile hydrochloride |
| 4 | 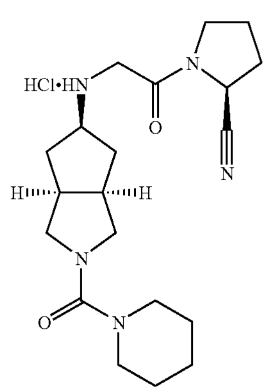 | cis-1-{2-[2-(Piperidine-1-carbonyl)-octahydro-cyclopenta[c]pyrrol-5-ylamino]-acetyl}-pyrrolidine-2-carbonitrile hydrochloride |

| Example No. | Structure | Name |
|---|---|---|
| 5 | 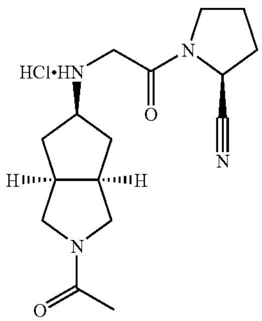 | cis-1-[2-(2-Acetyl-octahydro-cyclopenta[c]pyrrol-5-ylamino)-acetyl]-pyrrolidine-2-carbonitrile hydrochloride |
| 6 | 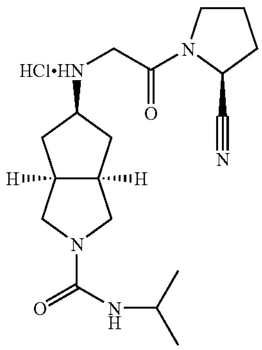 | cis-5-[2-(2-Cyano-pyrrolidin-1-yl)-2-oxo-ethylamino]-hexahydro-cyclopenta[c]pyrrole-2-carboxylic acid isopropylamide hydrochloride |
| 7 | 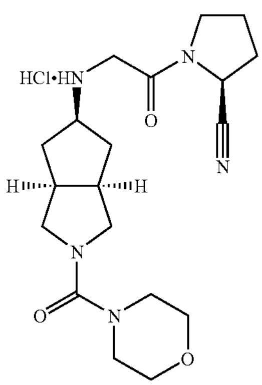 | cis-1-{2-[2-(Morpholine-4-carbonyl)-octahydro-cyclopenta[c]pyrrol-5-ylamino]-acetyl}-pyrrolidine-2-carbonitrile hydrochloride |
| 8 | 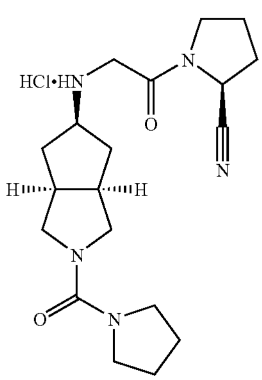 | cis-1-{2-[2-(Pyrrolidine-1-carbonyl)-octahydro-cyclopenta[c]pyrrol-5-ylamino]-acetyl}-pyrrolidine-2-carbonitrile hydrochloride |
| 9 | | cis-5-[2-(2-Cyano-pyrrolidin-1-yl)-2-oxo-ethylamino]-hexahydro-cyclopenta[c]pyrrole-2-carboxylic acid dimethylamide triflutate |
| 10 | | trans-5-[2-(2-Cyano-pyrrolidin-1-yl)-2-oxo-ethylamino]-hexahydro-cyclopenta[c]pyrrole-2-carboxylic acid dimethylamide triflutate |

Further, this invention relates to compounds of the following formula (I-1c) as intermediates in the synthesis of compounds having formula (I):

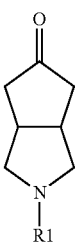

I-1c wherein:

$R_1$ is selected from the group consisting of hydrogen, alkyl, cycloalkyl, heterocyclo alkyl, aryl, heteroaryl, —C(O)NR$_3$R$_4$, —C(O)R$_3$ and —C(O)OR$_3$, wherein the alkyl, cycloalkyl, heterocycle alkyl, aryl or heteroaryl is further substituted with one or more groups selected from the group consisting of alkyl, aryl, hydroxyl, amino, alkoxyl, aryloxyl and heterocyclo alkyl;

$R_3$ and $R_4$ are each independently selected from the group consisting of hydrogen, alkyl, cycloalkyl, aryl, heteroaryl and heterocyclo alkyl, wherein the alkyl, cycloalkyl, aryl, heteroaryl or heterocyclo alkyl is further substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, cyano, hydroxyalkyl, heterocyclo alkyl, heterocyclo alkoxyl, trifluoromethyl, carboxylic acid and carboxylic ester; and $R_3$ and $R_4$ are attached together with the N atom to form a 3 to 8 membered hetero ring, wherein the 3 to 8 membered hetero ring further contains one or more heteroatoms selected from the group consisting of N, O and S atom, and the 3 to 8 membered rings are further substituted with one or more groups selected from the group consisting of alkyl, aryl, heteroaryl, haloalkyl, haloalkoxyl, hydroxyl, amino, cyano, alkoxyl, aryloxyl, hydroxyalkyl, heterocyclo alkyl, carboxylic acid, carboxylic ester, halogen and —$NR_3R_4$;

Furthermore, this invention relates to the preparation process of compounds of formula (IB), wherein the preparation process comprises the following steps of:

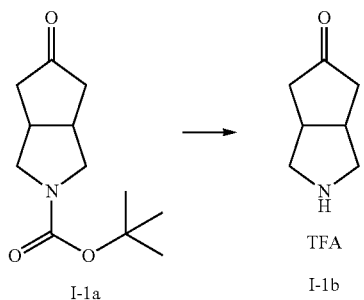

reacting starting material 5-oxo-hexahydro-cyclopenta[c]pyrrole-2-carboxylic acid tert-butyl ester (I-1a) with trifluoroacetic acid in the solvent of dichloromethane in an ice-water bath to obtain hexahydro-cyclopenta[c]pyrrol-5-one triflutate (I-1b);

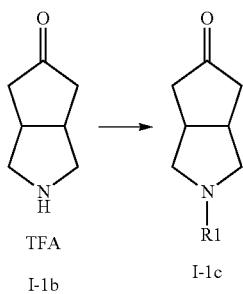

reacting hexahydro-cyclopenta[c]pyrrol-5-one triflutate (I-1b) with acyl chloride or ester, in the presence of base to give the compounds of formula (I-1c);

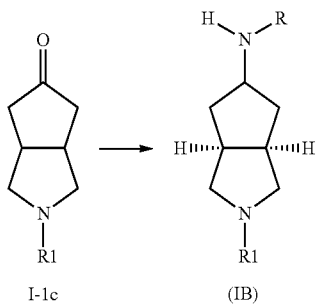

reacting the said compounds of formula (I-1c) with equivalent amounts of different amines, sodium triacetoxyborohydride and triethylamine in the solvent of methanol at room temperature to obtain the compounds of formula (IB);

wherein:

R is selected from the group consisting of alkyl, cycloalkyl, haloalkyl, aryl, heteroaryl, aminocarbonyl alkyl, amide alkyl, aminocarbonyl alkyl having heterocycle and aminoalkyl, wherein the heterocycle is 5- or 6-membered hetero ring further substituted with one or more groups selected from the group consisting of alkyl, aryl, heteroaryl, haloalkyl, haloalkoxyl, hydroxyl, amino, alkylamino, amide group, aminocarbonyl, cyano, alkynyl, alkoxyl, aryloxyl, aminoalkyl, hydroxyalkyl, heterocyclo alkyl, carboxylic acid, carboxylic ester and halogen;

$R_1$ is selected from the group consisting of hydrogen, alkyl, cycloalkyl, heterocyclo alkyl, aryl, heteroaryl, —C(O)$NR_3R_4$, —C(O)$R_3$ and —C(O)$OR_3$, wherein the alkyl, cycloalkyl, heterocyclo alkyl, aryl or heteroaryl is further substituted with one or more groups selected from the group consisting of alkyl, aryl, hydroxyl, amino, alkoxyl, aryloxyl and heterocyclo alkyl;

$R_3$ and $R_4$ are each independently selected from the group consisting of hydrogen, alkyl, cycloalkyl, aryl, heteroaryl and heterocyclo alkyl, wherein the alkyl, cycloalkyl, aryl, heteroaryl or heterocyclo alkyl is further substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, cyano, hydroxyalkyl, heterocyclo alkyl, heterocyclo alkoxyl, trifluoromethyl, carboxylic acid and carboxylic ester; and $R_3$ and $R_4$ are attached together with the N atom to form a 3 to 8 membered hetero ring, wherein the 3 to 8 membered hetero ring further contains one or more heteroatoms selected from the group consisting of N, O and S atom, and the 3 to 8 membered rings are further substituted with one or more groups selected from the group consisting of alkyl, aryl, heteroaryl, haloalkyl, haloalkoxyl, hydroxyl, amino, cyano, alkoxyl, aryloxyl, hydroxyalkyl, heterocyclo alkyl, carboxylic acid, carboxylic ester, halogen and —$NR_3R_4$;

Preferably, in the preparation process described above, R is the following formula:

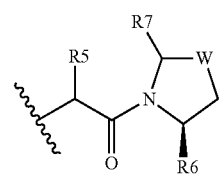

wherein:

$R_5$ is selected from the group consisting of hydrogen, alkyl, cycloalkyl, aryl, heteroaryl and heterocyclo alkyl, wherein the alkyl, cycloalkyl, aryl, heteroaryl or heterocyclo alkyl is further substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, alkylamino, cyano, hydroxyalkyl, heterocyclo alkyl, heterocyclo alkoxyl, carboxylic acid and carboxylic ester;

$R_6$ and $R_7$ are each independently selected from the group consisting of alkyl, aryl, heteroaryl, haloalkyl, haloalkoxyl, hydroxyl, amino, cyano, alkynyl, alkoxyl, aryloxyl, hydroxyalkyl, heterocyclo alkyl, carboxylic acid, carboxylic ester and halogen; and W is C, S or O atom.

Furthermore, this invention relates to a pharmaceutical composition comprising compounds or salts thereof having formula (I) in an effective therapeutic dose, as well as pharmaceutically acceptable carrier.

Furthermore, this invention relates to a use of the compounds or pharmaceutical acceptable salts having formula (I) in the preparation of a medicament as a dipeptidyl peptidase (DPPIV) inhibitor.

In other words, this invention is intended to provide the new aza-bicyclo alkane derivatives of formula (ID) and (IE) and tautomers, enantiomers, non-enantiomers, racemes, and pharmaceutically acceptable salts, and metabolites and metabolic precursors or prodrugs thereof.

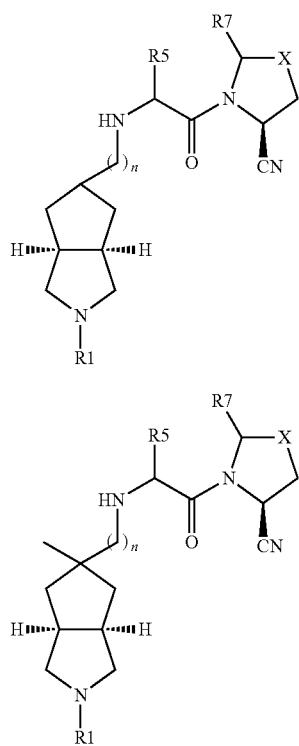

wherein:

$R_1$ is selected from the group consisting of hydrogen, alkyl, cycloalkyl, heterocyclo alkyl, aryl, heteroaryl, —C(O)NR$_3$R$_4$, —C(O)R$_3$ and —C(O)OR$_3$, wherein the alkyl, cycloalkyl, heterocyclo alkyl, aryl or heteroaryl is further substituted with one or more groups selected from the group consisting of alkyl, aryl, hydroxyl, amino, alkoxyl, aryloxyl and heterocyclo alkyl;

$R_3$ and $R_4$ are each independently selected from the group consisting of hydrogen, alkyl, cycloalkyl, aryl, heteroaryl and heterocyclo alkyl, wherein the alkyl, cycloalkyl, aryl, heteroaryl or heterocyclo alkyl is further substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, cyano, hydroxyalkyl, heterocyclo alkyl, heterocyclo alkoxyl, trifluoromethyl, carboxylic acid and carboxylic ester; and $R_3$ and $R_4$ are attached together with the N atom to form a 3 to 8 membered hetero ring, wherein the 3 to 8 membered hetero ring further contains one or more heteroatoms selected from the group consisting of N, O and S atom, and the 3 to 8 membered rings are further substituted with one or more groups selected from the group consisting of alkyl, aryl, heteroaryl, haloalkyl, haloalkoxyl, hydroxyl, amino, cyano, alkoxyl, aryloxyl, hydroxyalkyl, heterocyclo alkyl, carboxylic acid, carboxylic ester, halogen and —NR$_3$R$_4$;

n is an integer from 0 to 4;

$R_5$ is selected from the group consisting of hydrogen, alkyl, cycloalkyl, aryl, heteroaryl and heterocyclo alkyl, wherein the alkyl, cycloalkyl, aryl, heteroaryl or heterocyclo alkyl is further substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, alkylamino, cyano, hydroxyalkyl, heterocyclo alkyl, heterocyclo alkoxyl, carboxylic acid and carboxylic ester; and $R_7$ is each independently selected from the group consisting of alkyl, aryl, heteroaryl, haloalkyl, haloalkoxyl, hydroxyl, amino, cyano, alkynyl, alkoxyl, aryloxyl, hydroxyalkyl, heterocyclo alkyl, carboxylic acid, carboxylic ester and halogen.

Preferably, this invention relates to compounds or pharmaceutically acceptable salts of formula (IF) and (IG):

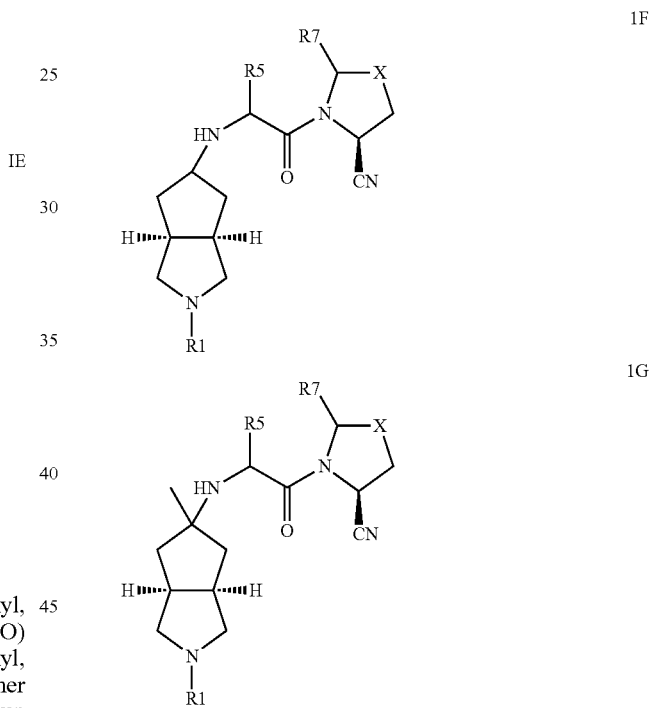

wherein:

$R_1$ is selected from the group consisting of hydrogen, alkyl, cycloalkyl, heterocyclo alkyl, aryl, heteroaryl, —C(O)NR$_3$R$_4$, —C(O)R$_3$ and —C(O)OR$_3$, wherein the alkyl, cycloalkyl, heterocyclo alkyl, aryl or heteroaryl is further substituted with one or more groups selected from the group consisting of alkyl, aryl, hydroxyl, amino, alkoxyl, aryloxyl and heterocyclo alkyl;

$R_3$ and $R_4$ are each independently selected from the group consisting of hydrogen, alkyl, cycloalkyl, aryl, heteroaryl and heterocyclo alkyl, wherein the alkyl, cycloalkyl, aryl, heteroaryl or heterocyclo alkyl is further substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, cyano, hydroxyalkyl, heterocyclo alkyl, heterocyclo alkoxyl, trifluoromethyl, carboxylic acid and carboxylic ester; and $R_3$ and $R_4$ are attached together with the N atom to form a 3 to 8 membered hetero ring, wherein the 3 to 8 membered hetero ring further contains one or more heteroatoms selected from the group consisting of N, O and S atom, and the 3 to 8 membered rings are further substituted with one or more groups selected from the group consisting of alkyl, aryl, heteroaryl, haloalkyl, haloalkoxyl, hydroxyl, amino, cyano, alkoxyl, aryloxyl, hydroxyalkyl, heterocyclo alkyl, carboxylic acid, carboxylic ester, halogen and —$NR_3R_4$;

$R_5$ is selected from the group consisting of hydrogen, alkyl, cycloalkyl, aryl, heteroaryl and heterocyclo alkyl, wherein the alkyl, cycloalkyl, aryl, heteroaryl or heterocyclo alkyl is further substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, alkylamino, cyano, hydroxyalkyl, heterocyclo alkyl, heterocyclo alkoxyl, carboxylic acid and carboxylic ester; and $R_7$ is each independently selected from the group consisting of alkyl, aryl, heteroaryl, haloalkyl, haloalkoxyl, hydroxyl, amino, cyano, alkynyl, alkoxyl, aryloxyl, hydroxyalkyl, heterocyclo alkyl, carboxylic acid, carboxylic ester and halogen.

Furthermore, this invention also relates to compounds of the following formula (I-1c) or (I-1g) as intermediates in the synthesis of compounds having formula (I):

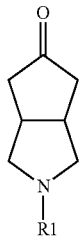

I-1c wherein:

$R_1$ is selected from the group consisting of hydrogen, alkyl, cycloalkyl, heterocyclo alkyl, aryl, heteroaryl, —C(O)$NR_3R_4$, —C(O)$R_3$ and —C(O)$OR_3$, wherein the alkyl, cycloalkyl, heterocyclo alkyl, aryl or heteroaryl is further substituted with one or more groups selected from the group consisting of alkyl, aryl, hydroxyl, amino, alkoxyl, aryloxyl and heterocyclo alkyl;

$R_3$ and $R_4$ are each independently selected from the group consisting of hydrogen, alkyl, cycloalkyl, aryl, heteroaryl and heterocyclo alkyl, wherein the alkyl, cycloalkyl, aryl, heteroaryl or heterocyclo alkyl is further substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, cyano, hydroxyalkyl, heterocyclo alkyl, heterocyclo alkoxyl, trifluoromethyl, carboxylic acid and carboxylic ester; and $R_3$ and $R_4$ are attached together with the N atom to form a 3 to 8 membered hetero ring, wherein the 3 to 8 membered hetero ring further contains one or more heteroatoms selected from the group consisting of N, O and S atom, and the 3 to 8 membered rings are further substituted with one or more groups selected from the group consisting of alkyl, aryl, heteroaryl, haloalkyl, haloalkoxyl, hydroxyl, amino, cyano, alkoxyl, aryloxyl, hydroxyalkyl, heterocyclo alkyl, carboxylic acid, carboxylic ester, halogen and —$NR_3R_4$;

This invention relates to compounds having formula (I) or pharmaceutically acceptable salts, wherein the compounds having formula (I) are in pharmaceutically acceptable free-form and the forms of acid addition salts, and provides the pharmaceutically acceptable (nontoxic, physiologically acceptable) salts thereof; wherein the pharmaceutically acceptable salts are selected from the group consisting of hydrochloride, p-toluenesulfonate, tartarate, maleate, lactate, methanesulfonate, sulfate, phosphate, citrate, acetate and triflutate. Preferably, the salts are p-toluenesulfonate, hydrochloride and trifluoroacetate. More preferably, the salts are hydrochloride and triflutate.

DETAILED DESCRIPTION OF THE INVENTION

Unless otherwise stated, the following terms used in the specification and claims have the meanings discussed below.

"Alkyl" refers to a saturated aliphatic hydrocarbon group including $C_1$-$C_{20}$ straight chain and branched chain groups. Preferably an alkyl group is a middle size alkyl having 1 to 10 carbon atoms, e.g., methyl, ethyl, propyl, 2-propyl, n-butyl, iso-butyl, tert-butyl, pentyl, and the like. More preferably, it is a lower alkyl having 1 to 4 carbon atoms, e.g., methyl, ethyl, propyl, 2-propyl, n-butyl, iso-butyl, or tert-butyl, and the like. The alkyl group may be substituted or unsubstituted. When substituted, the substituent group(s) is preferably independently halo, hydroxyl, lower alkoxy, aryl, aryloxy, heteroaryl, heterocyclo alkyl, C(O)$R_3$ and C(O)$NR_3R_4$.

"Cycloalkyl" refers to a 3 to 8 membered all-carbon monocyclic ring, an all-carbon 5-membered/6-membered or 6-membered/6-membered fused bicyclic ring or a multicyclic fused ring (a "fused" ring system means that each ring in the system shares an adjacent pair of carbon atoms with other ring in the system) group wherein one or more rings may contain one or more double bonds, but none of the rings has a completely conjugated pi-electron system. Examples of cycloalkyl groups are cyclopropane, cyclobutane, cyclopentane, cyclopentene, cyclohexane, cyclohexadiene, adamantane, cycloheptane, cycloheptatriene, and the like. The cycloalkyl group may be substituted or unsubstituted. When substituted, the substituent group(s) is preferably one or more independently selected from the group consisting of lower alkyl, trihaloalkyl, halo, hydroxy, lower alkoxy, aryl (optionally substituted with one or more groups which each independently is halo, hydroxy, lower alkyl or lower alkoxy groups), aryloxy (optionally substituted with one or more groups which each independently is halo, hydroxy, lower alkyl or lower alkoxy groups), 6-membered heteroaryl (having 1 to 3 nitrogen atoms on the ring, the carbons on the ring being optionally substituted with one or more groups which each independently is halo, hydroxy, lower alkyl or lower alkoxy groups), 5-membered heteroaryl (having 1 to 3 heteroatoms selected from the group consisting of nitrogen, oxygen and sulfur, the carbon and nitrogen atoms of the group being optionally substituted with one or more groups which each independently is halo, hydroxy, lower alkyl or lower alkoxy groups), 5- or 6-membered hetercyclo alkyl (having 1 to 3 heteroatoms selected from the group consisting of nitrogen, oxygen and sulfur, the carbon and nitrogen (if present) atoms of the group being optionally substituted with one or more groups which each independently is halo, hydroxy, lower alkyl or lower alkoxy groups), mercapto, (lower alkyl) thio, arylthio (optionally substituted with one or more groups which each independently is halo, hydroxy, lower alkyl or lower alkoxy groups), cyano, acyl, thioacyl, O-carbamyl, N-carbamyl, O-thiocarbamyl, N-thiocarbamyl, C-amido, N-amido, nitro, N-sulfonamido, S-sulfonamido, C(O)$R_3$, C(O)$NR_3R_4$ and —C(O)$OR_3$.

"Alkenyl" refers to an alkyl group as defined above having at least 2 carbon atoms and at least one carbon-carbon double bond. Representative examples include, but are not limited to ethenyl, 1-propenyl, 2-propenyl, 1-, 2-, 3-butenyl, and the like.

"Alkynyl" refers to an alkyl group as defined above having at least 2 carbon atoms and at least one carbon-carbon triple bond. Representative examples include, but are not limited to ethynyl, 1-propynyl, 2-propynyl, 1-, 2-, 3-butynyl, and the like.

"Aryl" refers to groups having at least one aromatic ring, i.e., having a conjugated pi-electron system, including all-carbon cyclic aryl, heteroaryl and biaryl group. Said aryl group may be optionally substituted with one or more groups each independently selected from the group consisting of halo, trihalomethyl, hydroxy, SR, nitro, cyano, alkoxyl and alkyl.

"Heteroaryl" refers to an aryl having 1 to 3 heteroatoms selected from the group consisting of N, O, and S as ring atoms, the remaining ring atoms being C. Said ring is 5- or 6-membered ring. The examples of heteroaryl groups include furyl, thienyl, pyridyl, pyrrolyl, N-alkyl pyrrolyl, pyrimidinyl, pyrazinyl, imidazolyl, and the like.

"Heterocyclo alkyl" refers to a monocyclic or fused ring group of 5 to 9 ring atoms, wherein one, or two ring heteroatoms are selected from the group consisting of N, O, and S(O)n (n is integer from 0 to 2), the remaining ring atoms are C, in addition, the ring may also have one or more double bonds, but not have a completely conjugated pi-electron system. The unsubstituted heterocyclo alkyl includes, but is not limited to pyrrolidyl, piperidine subbase, piperazine subbase, morpholinyl, thiomorpholinyl, homopiperazinyl, and the like. The heterocyclo alkyl may be substituted or unsubstituted. When substituted, the substituent is preferably one or more, more preferably one, two, or three, further more preferably one or two groups, each independently selected from the group consisting of lower alkyl, trihaloalkyl, halo, hydroxy, lower alkoxy, cyano and acyl. Preferably, the heterocyclo alkyl is optionally substituted with one or two groups independently selected from the group consisting of halo, lower alkyl, trihaloalkyl, hydroxy, mercapto, cyano, N-amido, and carboxy.

"Hydroxy" refers to an —OH group.

"Alkoxyl" refers to both an —O-(alkyl) and an —O-(unsubstituted cycloalkyl) group. Representative examples include, but are not limited to, e.g., methoxy, ethoxy, propoxy, butoxy, cyclopropyloxy, cyclobutyloxy, cyclopentyloxy, cyclohexyloxy, and the like.

"Haloalkoxy" refers to an —O-(haloalkyl). Representative examples include, but are not limited to, e.g., trifluoromethoxy, tribromomethoxy, and the like.

"Aryloxyl" refers to both an —O-aryl and an —O-heteroaryl group, wherein the aryl and heteroaryl are as defined above. Representative examples include, but are not limited to, e.g., phenoxy, pyridinyloxy, furanyloxy, thienyloxy, pyrimidinyloxy, pyrazinyloxy, and the like, and derivatives thereof.

"Mercapto" refers to a —SH group.

"Alkylthio" refers to a —S-(alkyl) and a —S-(unsubstituted cycloalkyl) group. Representative examples include, but are not limited to, e.g., methylthio, ethylthio, propylthio, butylthio, cyclopropylthio, cyclobutylthio, cyclopentylthio, cyclohexylthio, and the like.

"Arylthio" refers to a —S-aryl and a —S-heteroaryl group, wherein the aryl and heteroaryl are as defined above. Representative examples include, but are not limited to, e.g., phenylthio, pyridinylthio, furanylthio, thienylthio, pyrimidinylthio, and the like, and derivatives thereof.

"Acyl" refers to a —C(O)—R" group, where R" is selected from the group consisting of hydrogen, lower alkyl, trihalomethyl, unsubstituted cycloalkyl, aryl (optionally substituted with one or more, preferably one, two, or three substituents selected from the group consisting of lower alkyl, trihalomethyl, lower alkoxy and halo groups), heteroaryl (bonded through a ring carbon) (optionally substituted with one or more, preferably one, two, or three substitutents selected from the group consisting of lower alkyl, trihaloalkyl, lower alkoxy and halo groups), and heteroalicyclic (bonded through a ring carbon) (optionally substituted with one or more, preferably one, two, or three substituents selected from the group consisting of lower alkyl, trihaloalkyl, lower alkoxy and halo groups). Representative acyl groups include, but are not limited to, acetyl, trifluoroacetyl, benzoyl, and the like.

"Thioacyl" refers to a —C(S)—R" group, wherein R" is as defined above.

"Acetyl" refers to a —C(O)CH$_3$ group.

"Halo" refers to fluoro, chloro, bromo, or iodo, preferably fluoro or chloro.

"Trifluoromethyl" refers to a —CF$_3$ group.

"Cyano" refers to a —C≡N group.

"Amino" refers to a —NH$_2$ group.

"Carboxylic acid" refers to a —COOH group.

"Carboxylic ester" refers to a —COOR group, wherein R is alkyl or cycloalkyl.

"Hydroxyl alkyl" refers to a —(CH$_2$)rNH$_2$ group, wherein r is an integer from 1 to 4.

"Optional" or "optionally" means that the subsequently described event or circumstance may or may not occur, and that the description includes instances where the event or circumstance may or may not occur. For example, "heterocycle group optionally substituted with an alkyl group" means that the alkyl may or may not be present, and the description includes situations where the heterocycle group is substituted with an alkyl group and situations where the heterocyclo group is not substituted with the alkyl group.

A "pharmaceutical composition" refers to a mixture of one or more of the compounds described herein, or physiologically/pharmaceutically acceptable salts or prodrugs thereof, with other chemical components, such as physiologically/pharmaceutically acceptable carriers and excipients. The purpose of a pharmaceutical composition is to facilitate administration of a compound to an organism.

Synthesis Method of the Invention Compound

In order to complete the objective of the invention, the invention applies the following technical solution:

A preparation process of compounds of formula (IB) or pharmaceutically acceptable salts of the invention, comprising the following steps of:

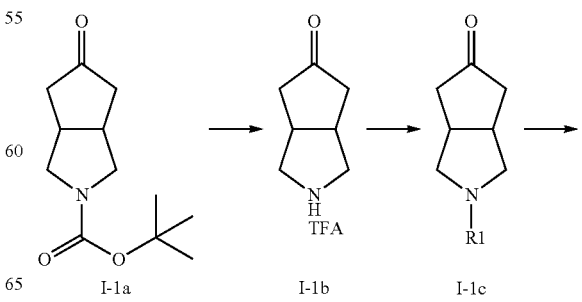

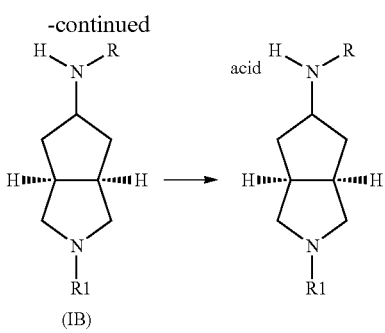

Reacting starting material 5-oxo-hexahydro-cyclopenta[c]pyrrole-2-carboxylic acid tert-butyl ester (I-1a) with trifluoroacetic acid in the solvent of dichloromethane in an ice-water bath to obtain hexahydro-cyclopenta[c]pyrrol-5-one triflutate (I-1b); reacting hexahydro-cyclopenta[c]pyrrol-5-one triflutate (I-1b) with acyl chloride or ester in the presence of base to give the compounds of formula (I-1c); reacting the compounds of formula (I-1c) with equivalent amounts of different amines, sodium triacetoxyborohydride and triethylamine in the solvent of methanol at room temperature to obtain the compounds of formula (IB).

This invention relates to a pharmaceutical composition comprising a compound or salt having formula (I) in an effective therapeutic dose, as well as a pharmaceutically acceptable carrier, or this invention relates to a use of the compounds or salts in the preparation of a medicament as a dipeptidyl peptidase inhibitor. In other words, this invention also provides the composition comprising the above compound in an effective therapeutic dose, and the use of the compounds in the preparation of a medicament as a dipeptidyl peptidase inhibitor.

Specific Implemention Methods

The following examples serve to illustrate the invention, but the examples should not be considered as limiting the scope of the invention.

EXAMPLES

The compound's structure determination was confirmed by NMR and MS. NMR chemical shifts were given in ppm ($10^{-6}$). NMR was determined by a Bruker AVANCE-400 machine. The solvent were deuterated-chloroform ($CDCl_3$) and deuterated-dimethyl sulfoxide (DMSO-d6) with tetramethylsilane (TMS) as internal standard. Chemical shifts were given in ppm ($10^{-6}$).

MS was determined by a FINNIGAN LCQ Ad (ESI) mass spectrometer.

The average of inhibitory rate of kinase and $IC_{50}$ was determined by a NovoStar ELIASA (BMG Co. German).

Thin-layer silica gel was yantai huanghai HSGF254 or qingdao GF254 silica gel plate.

Column chromatography generally used yantai huanghai 200-300 mesh silica gel as carrier.

DMSO-$D_6$: deuterated-dimethyl sulfoxide.

$CDCl_3$: deuterated-chloroform.

Example 1 cis-5-[2-(2-Cyano-pyrrolidin-1-yl)-2-oxo-ethylamino]-hexahydro-cyclopenta[c]pyrrole-2-carboxylic acid dimethylamide hydrochloride

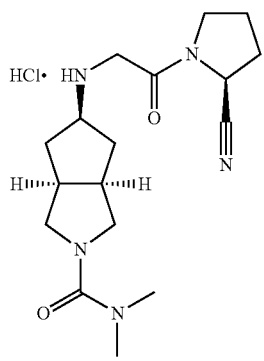

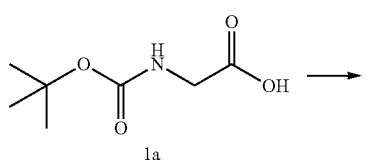

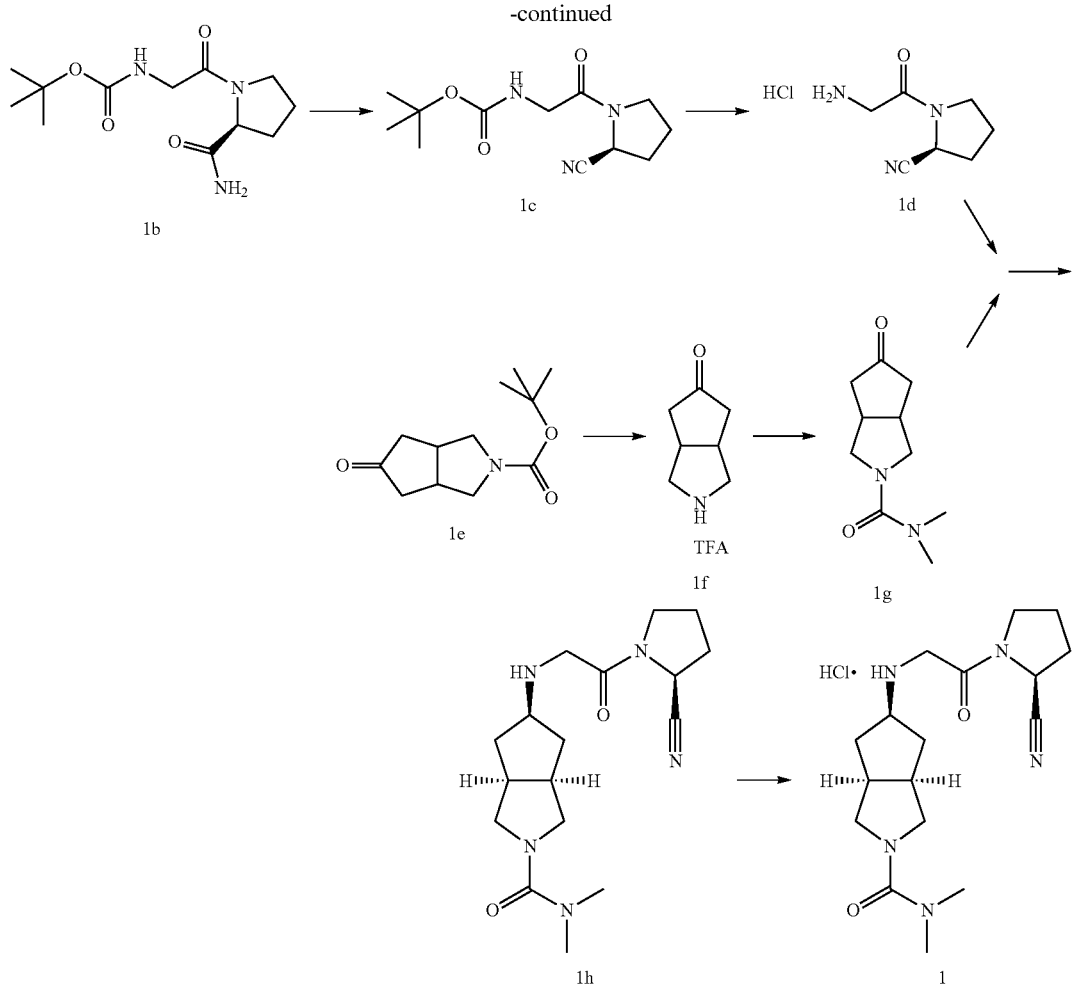

Preparation of [2-(2-carbamoyl-pyrrolidin-1-yl)-2-oxo-ethyl]-carbamic acid tert-butyl ester 1b N-tert-butyloxycarbonyl glycine 1a (5 g, 28.56 mmol) and L-prolinamide (3.25 g, 28.50 mmol) were dissolved in 75 mL of N,N-dimethylformamide, the resulting solution was cooled down to 0° C. (centigrade), and 1-hydroxybenzotriazole (11.8 g, 87.3 mmol), N-ethyl-N'-(dimethylaminopropyl)-carbodiimide (11.3 g, 59 mmol) and triethylamine (12.1 mL, 87.3 mmol) were then added with stirring. Upon completion of the addition, the reaction mixture was allowed to increase to room temperature, and stirred overnight. After thin lay chromatography showed the starting material disappeared, N,N-dimethylformamide was evaporated below 50° C., and the reaction solution was extracted with ethyl acetate (200 mL×3). The combined organic extracts were washed with 50 mL of saturated brine, dried over anhydrous sodium sulfate, filtered and concentrated under reduced pressure. The residue was purified by recrystallization with ethyl acetate to obtain the title compound [2-(2-carbamoyl-pyrrolidin-1-yl)-2-oxo-ethyl]-carbamic acid tert-butyl ester 1b (7.42 g, yield 95.8%) as a white powder.

MS m/z (ESI): 272.1(M+1)

Preparation of [2-(2-cyano-pyrrolidin-1-yl)-2-oxo-ethyl]-carbamic acid tert-butyl ester 1c In a dry three-neck flask under a nitrogen atmosphere, 286 mL of pyridine, [2-(2-carbamoyl-pyrrolidin-1-yl)-2-oxo-ethyl]-carbamic acid tert-butyl ester 1b (13.5 g, 49.8 mmol) and imidazole (7.11 g, 104.6 mmol) were added successively. The reaction system was cooled down to −35° C., and phosphorus oxychloride (19 mL, 204.2 mmol) was then added dropwise to the solution with stirring. After stirring for 1 hour at −35° C., the reaction mixture was allowed to increase to room temperature, and stirred for another 0.5 hour. Pyridine was evaporated under low temperature, and the reaction mixture was diluted with water, then extracted with ethyl acetate (200 mL×3). The combined organic extracts were washed with 50 mL of saturated brine, dried over anhydrous sodium sulfate, filtered and concentrated under reduced pressure. The residue was purified by silica gel column chromatography to obtain the title compound [2-(2-cyano-pyrrolidin-1-yl)-2-oxo-ethyl]-carbamic acid tert-butyl ester 1e (10.7 g, yield 84.9%) as a white powder.

MS m/z (ESI): 254.3(M+1)

Preparation of 1-(2-amino-acetyl)-pyrrolidine-2-carbonitrile hydrochloride 1d

[2-(2-Cyano-pyrrolidin-1-yl)-2-oxo-ethyl]-carbamic acid tert-butyl ester 1e (13.7 g, 54.2 mmol) was dissolved in the solvent mixture of 140 mL of ether and 40 mL of water, and 37% hydrochloride acid (90 mL) were then added dropwise to the solution. Upon completion of the addition, the reaction mixture was stirred for 1 hour in an ice-water bath, the solvent was evaporated, and ether was added to the residue to centrifuge to give 1-(2-amino-acetyl)-pyrrolidine-2-carbonitrile hydrochloride 1d (10 g, yield 98%) as a white powder.

MS m/z (ESI): 154.4(M+1)

Preparation of
hexahydro-cyclopenta[c]pyrrole-5-one triflutate 1f 5-oxo-hexahydro-cyclopenta[c]pyrrole-2-carboxylic acid tert-butyl ester 1e (0.32 g, 1.42 mmol) was dissolved in 10 mL of dichloromethane, and trifluoroacetic acid (3.27 mL, 42.7 mmol) was then added to the solution in an ice-water bath. Upon completion of the addition, the reaction mixture was stirred at 0° C. for 30 minutes, then the solvent was evaporated to dryness to obtain the title compound hexahydro-cyclopenta[c]pyrrol-5-one triflutate 1f which was directly used in the further reaction.

MS m/z (ES!): 126.4(M+1)

Preparation of
5-oxo-hexahydro-cyclopenta[c]pyrrole-2-carboxylic acid dimethylamide 1g The crude product of hexahydro-cyclopenta[c]pyrrole-5-one triflutate 1f obtained above was dissolved in 15 mL of acetonitrile, and potassium carbonate (0.24 g, 1.71 mmol) was then added to the solution in an ice-water bath, followed by N,N-dimethylcarbamic chloride (0.14 mL, 1.56 mmol). Upon completion of the addition, the reaction mixture was allowed to increase to room temperature, and stirred for 2 hours, the solvent was evaporated, and 50 mL of water was then added to the residue. The mixture was extracted with ethyl acetate (50 mL×3). The combined organic extracts were washed with 50 mL of saturated brine, dried over anhydrous magnesium sulfate, filtered and concentrated under reduced pressure. The residue was purified by silica gel column chromatography to obtain the title compound 5-oxo-hexahydro-cyclopenta[c]pyrrole-2-carboxylic acid dimethylamide 1g (0.19 g, yield 68.3%) as a light yellow oil.

MS m/z (ESI): 197.4(M+1)

Preparation of cis-5-[2-(2-cyano-pyrrolidin-1-yl)-2-oxo-ethylamino]-hexahydro-cyclopenta[c]pyrrole-2-carboxylic acid dimethylamide 1h 1-(2-Amino-acetyl)-pyrrolidine-2-carbonitrile hydrochloride 1d (0.36 g, 1.91 mmol) was dissolved in 20 mL of methanol, and 5-oxo-hexahydro-cyclopenta[c]pyrrole-2-carboxylic acid dimethylamide 1g (0.25 g, 1.28 mmol) and sodium triacetoxyborohydride (1.22 g, 5.74 mmol) were then added to the solution with stirring. After stirring for 3 hours at room temperature, the resulting mixture was concentrated, and 20 mL of saturated sodium carbonate solution was then added to the mixture. The reaction mixture was extracted with dichloromethane (20 mL×10). The combined organic extracts were washed with 10 mL of saturated brine, dried over anhydrous sodium sulfate, filtered and concentrated under reduced pressure. The residue was purified by silica gel column chromatography to give the title compound cis-5-[2-(2-cyano-pyrrolidin-1-yl)-2-oxo-ethylamino]-hexahydro-cyclopenta[c]pyrrole-2-carboxylic acid dimethylamide 1h (0.3 mg, yield 53%) as a white powder.

MS m/z (ESI): 334.5(M+1)

Preparation of cis-5-[2-(2-cyano-pyrrolidin-1-yl)-2-oxo-ethylamino]-hexahydro-cyclopenta[c]pyrrole-2-carboxylic acid dimethylamide hydrochloride 1 cis-5-[2-(2-Cyano-pyrrolidin-1-yl)-2-oxo-ethylamino]-hexahydro-cyclopenta[c]pyrrole-2-carboxylic acid dimethylamide 1h (200 mg, 0.687 mmol) was dissolved in 10 mL of dichloromethane, and a solution of 0.5 N hydrochloride acid in 2 mL of ether was then added to the solution in an ice-water bath. The solvent was evaporated to dryness, and 10 mL of ether was then added to the residue. The resulting precipitate was centrifuged to give the title compound cis-5-[2-(2-cyano-pyrrolidin-1-yl)-2-oxo-ethylamino]-hexahydro-cyclopenta[c]pyrrole-2-carboxylic acid dimethylamide hydrochloride 1 (180 mg, yield 80%) as a white powder.

$^1$H NMR (CD$_3$OD, 400 MHz) δ 4.82(dd, 1H, J$_1$=4 Hz, J$_2$=5.2 Hz), 4.02 (dd, 2H, J$_1$=J$_2$=16.4 Hz), 3.62-3.25(m, 7H), 2.76(s, 6H), 2.51-1.49(m, 10H).

Example 2 cis-5-[2-(2-Cyano-pyrrolidin-1-yl)-2-oxo-ethylamino]-hexahydro-cyclopenta[c]pyrrole-2-carboxylic acid methyl ester hydrochloride

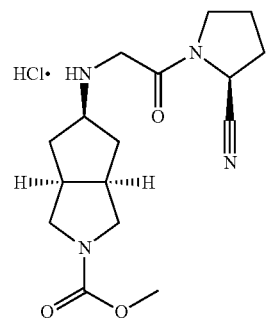

2

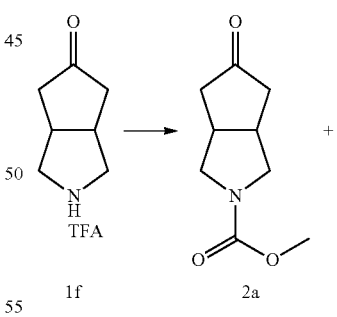

1f        2a

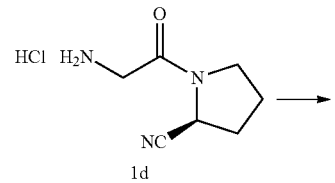

1d

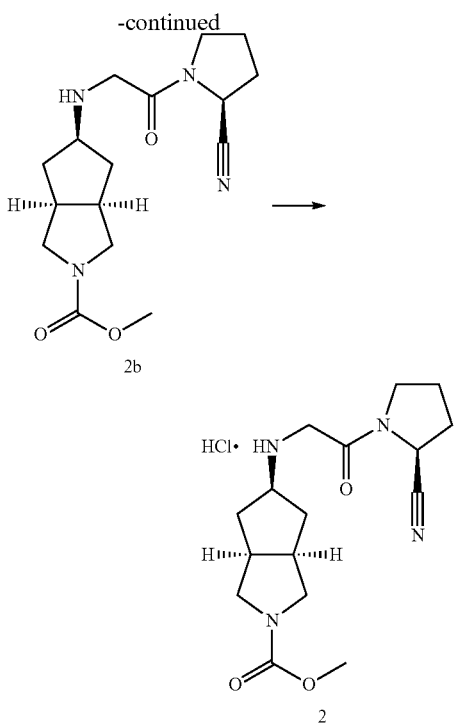

Preparation of 5-oxo-hexahydro-cyclopenta[c]pyrrole-2-carboxylic acid methyl ester 2a Hexahydro-cyclopenta[c]pyrrol-5-one triflutate 1f (0.559 g, 2.34 mmol) was dissolved in 20 mL of acetonitrile, and potassium carbonate (0.646 g, 4.68 mmol) and methyl chloroformate (0.22 mL, 2.8 mmol) were then added to the solution in an ice-water bath successively. Upon completion of the addition, the reaction mixture was allowed to increase to room temperature, and stilled overnight. The solvent was evaporated, and 50 mL of water was then added to the residue. The mixture was extracted with ethyl acetate (50 mL×3). The combined organic extracts were washed with 50 mL of saturated brine and 50 mL of water successively, dried over anhydrous magnesium sulfate, filtered and concentrated under reduced pressure. The residue was purified by silica gel column chromatography to obtain the title compound 5-oxo-hexahydro-cyclopenta[c]pyrrole-2-carboxylic acid methyl ester 2a (0.25 g, yield 58.4%) as a colorless oil.

MS m/z (ESI): 184(M+1)

Preparation of cis-5-[2-(2-cyano-pyrrolidin-1-yl)-2-oxo-ethylamino]-hexahydro-cyclopenta[c]pyrrole-2-carboxylic acid methyl ester 2b 1-(2-Amino-acetyl)-pyrrolidine-2-carbonitrile hydrochloride 1d (0.43 g, 2.29 mmol) was dissolved in 20 mL of methanol, and 5-oxo-hexahydro-cyclopenta[c]pyrrole-2-carboxylic acid methyl ester 2a (0.28 g, 1.53 mmol) and sodium triacetoxyborohydride (1.46 g, 6.88 mmol) were then added to the solution with stirring. After stirring for 3 hours at room temperature, the reaction mixture was concentrated, then saturated sodium carbonate solution (20 mL) was added to the mixture. The reaction mixture was extracted with dichloromethane (20 mL×3). The combined organic extracts were washed with 10 mL of saturated brine, dried over anhydrous sodium sulfate, filtered and concentrated under reduced pressure. The residue was purified by silica gel column chromatography to obtain cis-5-[2-(2-cyano-pyrrolidin-1-yl)-2-oxo-ethylamino]-hexahydro-cyclopenta[c]pyrrole-2-carboxylic acid methyl ester 2b (0.22 g, yield 41%) as a white powder.

MS m/z (ESI): 357(M+1)

Preparation of cis-5-[2-(2-cyano-pyrrolidin-1-yl)-2-oxo-ethylamino]-hexahydro-cyclopenta[c]pyrrole-2-carboxylic acid methyl ester hydrochloride 2 cis-5-[2-(2-Cyano-pyrrolidin-1-yl)-2-oxo-ethylamino]-hexahydro-cyclopenta[c]pyrrole-2-carboxylic acid methyl ester 2b (200 mg, 0.687 mmol) was dispersed in 10 mL of ether, and a solution of 0.5 N hydrochloride acid in 2 mL of ether was then added to the solution in an ice-water bath. The precipitate was centrifuged to obtain the title compound cis-5-[2-(2-cyano-pyrrolidin-1-yl)-2-oxo-ethylamino]-hexahydro-cyclopenta[c]pyrrole-2-carboxylic acid methyl ester hydrochloride 2 (200 mg) as a white powder.

$^1$H NMR (CD$_3$OD, 400 MHz) δ 4.71(m, 1H), 3.93(m, 2H), 3.59-3.28(m, 10H), 2.64(m, 2H), 2.34(m, 2H), 2.17(m, 2H), 2.08(m, 2H).

Example 3 cis-1-{2-[2-(2-Hydroxy-acetyl)-octahydro-cyclopenta[c]pyrrol-5-ylamino]-acetyl}-pyrrolidine-2-carbonitrile hydrochloride

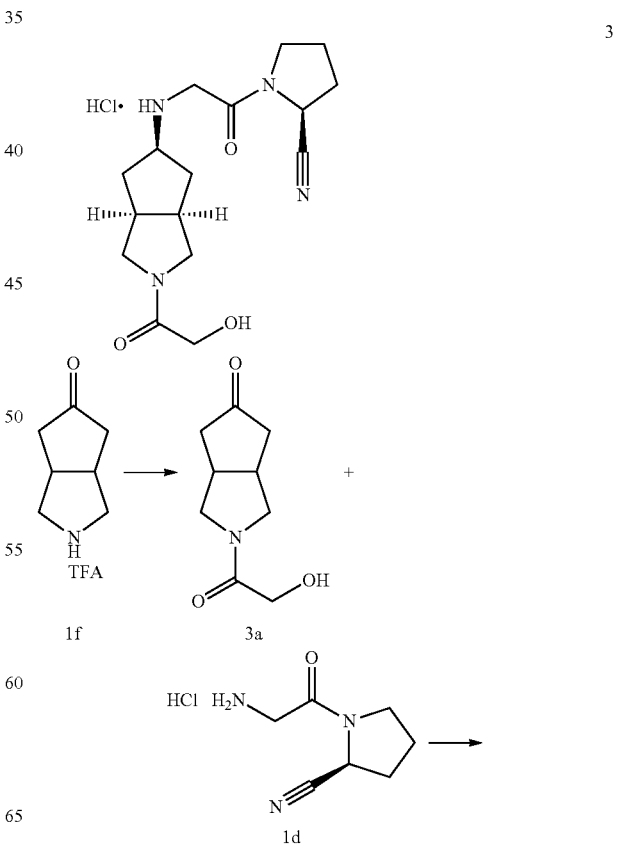

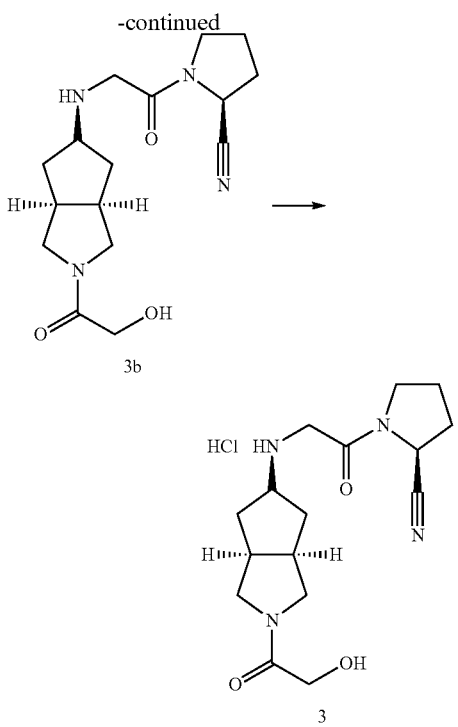

fied by silica gel column chromatography to give the title compound cis-1-{2-[2-(2-hydroxy-acetyl)-octahydro-cyclopenta[c]pyrrol-5-ylamino]-acetyl}-pyrrolidine-2-carbonitrile 3b which was directly used in the further reaction.

MS m/z (ESI): 357(M+1)

Preparation of cis-1-{2-[2-(2-hydroxy-acetyl)-octahydro-cyclopenta[c]pyrrol-5-ylamino]-acetyl}-pyrrolidine-2-carbonitrile hydrochloride 3 cis-1-{2-[2-(2-Hydroxy-acetyl)-octahydro-cyclopenta[c]pyrrol-5-ylamino]-acetyl}-pyrrolidine-2-carbonitrile 3b was dispersed in 10 mL of ether, and a solution of 0.5 N hydrochloride acid in 2 mL of ether was then added to the solution in an ice-water bath. The precipitate was centrifuged to obtain the title compound cis-1-{2-[2-(2-hydroxy-acetyl)-octahydro-cyclopenta[c]pyrrol-5-ylamino]-acetyl}-pyrrolidine-2-carbonitrile hydrochloride 3 (100 mg) as a white powder.

Example 4 cis-1-{2-[2-(Piperidine-1-carbonyl)-octahydro-cyclopenta[c]pyrrol-5-ylamino]-acetyl}-pyrrolidine-2-carbonitrile hydrochloride Preparation of 2-(2-hydroxy-acetyl)-hexahydro-cyclopenta[c]pyrrol-5-one 3a Hexahydro-cyclopenta[c]pyrrol-5-one triflutate 1f (764.8 mg, 3.2 mmol) and 2-hydroxyacetic acid (267.5 mg, 3.52 mmol) were dissolved in 10 mL of acetonitrile, and hydroxyacetic acid (1.3 g, 9.6 mmol), 1-ethyl-3-dimethylaminopropyl-carbodiimide hydrochloride (1.23 g, 6.4 mmol) and triethylamine (1.3 mL, 9.6 mmol) were then added to the solution in an ice-water bath. The ice-water bath was then removed, and the reaction mixture was stirred overnight at 25° C. The solvent was evaporated, and 20 mL of ethyl acetate was then added to the residue. The mixture was filtered and the filtrate was washed with 20 mL of water. The combined organic extracts were dried over anhydrous magnesium sulfate, filtered and concentrated under reduced pressure. The residue was purified by silica gel column chromatography to obtain the title compound 2-(2-hydroxy-acetyl)-hexahydro-cyclopenta[c]pyrrol-5-one 3a (0.375 g, yield 64%) as a colorless oil.

MS m/z (ESI): 184(M+1)

Preparation of cis-1-{2-[2-(2-hydroxy-acetyl)-octahydro-cyclopenta[c]pyrrol-5-ylamino]-acetyl}-pyrrolidine-2-carbonitrile 3b 2-(2-Hydroxy-acetyl)-hexahydro-cyclopenta[c]pyrrol-5-one 3a (0.375 g, 2.05 mmol) and 1-(2-amino-acetyl)-pyrrolidine-2-carbonitrile hydrochloride 1d (0.78 g, 4.1 mmol) were dissolved in the solvent mixture of 5 mL of methanol and 10 mL of sodium triacetoxyborohydride (0.87 g, 4.1 mmol) was then added to the mixture, and the mixture was stirred overnight at room temperature. The resulting mixture was concentrated under reduced pressure, and methanol (50 mL) and potassium carbonate (2 g, 7 mmol) were then added to the mixture. After 0.5 hour's stirring, the mixture was filtered and concentrated under reduced pressure. The residue was puri-

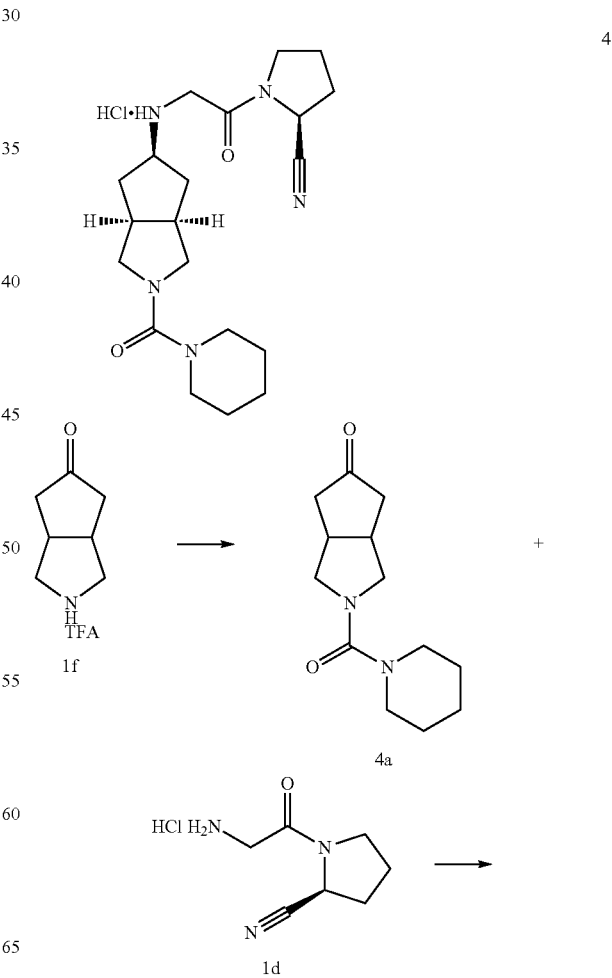

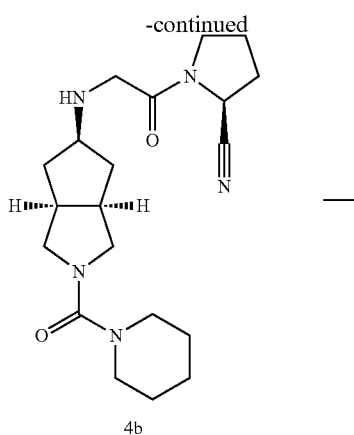

4b

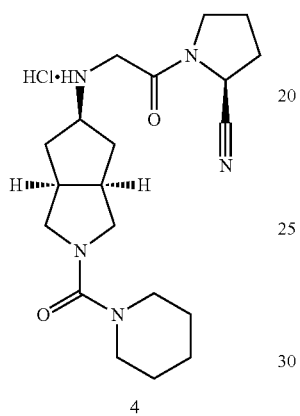

4

Preparation of 2-(piperidine-1-carbonyl)-hexahydro-cyclopenta[c]pyrrol-5-one 4a

Hexahydro-cyclopenta[c]pyrrol-5-one triflutate 1f (478 mg, 2 mmol) was dissolved in 20 mL of dichloromethane, and 1-methyl-3-(piperidine-1-carbonyl)-1H-imidazol-3-ium iodide (0.96 g, 3 mmol) and triehtylamine (0.84 mL, 6 mmol) were then added to the solution. Upon completion of the addition, the reaction mixture was stirred overnight at room temperature, 20 mL of water was then added to the mixture to quech the reaction, and the mixture was extracted with dichloromethane (50 mL×3). The combined organic extracts were washed with 10% citric acid solution (50 mL) and 50 mL of saturated brine successively, dried over anhydrous magnesium sulfate, filtered and concentrated under reduced pressure. The residue was purified by silica gel column chromatography to obtain the title compound 2-(piperidine-1-carbonyl)-hexahydro-cyclopenta[c]pyrrol-5-one 4a (0.41 g, yield 87%) as a colorless oil.

MS m/z (ESI): 237(M+1)

Preparation of cis-1-{2-[2-(piperidine-1-carbonyl)-octahydro-cyclopenta[c]pyrrol-5-ylamino]-acetyl}-pyrrolidine-2-carbonitrile 4b 2-(Piperidine-1-carbonyl)-hexahydro-cyclopenta[c]pyrrol-5-one 4a (0.41 g, 1.74 mmol) and 1-(2-amino-acetyl)-pyrrolidine-2-carbonitrile hydrochloride 1d (0.5 g, 2.6 mmol) were dissolved in 50 mL of tetrahydrofuran, and sodium sulfate (5 g) and acetic acid (0.05 mL) were then added to the solution. Upon completion of the addition, the reaction mixture was stirred for 0.5 hour at room temperature, sodium triacetoxyborohydride (1.1 g, 5.2 mmol) was then added to the mixture, and the mixture was stirred for 3 hours at room temperature. The reaction mixture was concentrated under reduced pressure, and saturated sodium carbonate solution (50 mL) was then added to the mixture. The reaction mixture was extracted with ethyl acetate (50 mL×3). The combined organic extracts were washed with 50 mL of saturated brine and 50 mL of water successively, dried over anhydrous magnesium sulfate, filtered and concentrated under reduced pressure. The residue was purified by silica gel column chromatography to obtain the title compound cis-1-{2-[2-(piperidine-1-carbonyl)-octahydro-cyclopenta[c]pyrrol-5-ylamino]-acetyl}-pyrrolidine-2-carbonitrile 4b which was directly used in the further reaction.

MS m/z (ESI): 410(M+1)

Preparation of cis-1-{2-[2-(piperidine-1-carbonyl)-octahydro-cyclopenta[c]pyrrol-5-ylamino]-acetyl}-pyrrolidine-2-carbonitrile hydrochloride 4 cis-1-{2-[2-(Piperidine-1-carbonyl)-octahydro-cyclopenta[c]pyrrol-5-ylamino]-acetyl}-pyrrolidine-2-carbonitrile 4b was dispersed in 10 mL of ether, and a solution of 0.5 N hydrochloride acid in 2 mL of ether was then added to the solution in an ice-water bath. The precipitate was centrifuged to obtain the title compound cis-1-{2-[2-(piperidine-1-carbonyl)-octahydro-cyclopenta[c]pyrrol-5-ylamino]-acetyl}-pyrrolidine-2-carbonitrile hydrochloride 4 (0.16 g) as a white powder.

$^1$H NMR (CD$_3$OD, 400 MHz) δ 4.83(dd, 1H, J$_1$=3.0 Hz, J$_2$=5.8 Hz), 4.09 (dd, 2H, J$_1$=J$_2$=13.1 Hz), 3.70-3.30(m, 10H), 2.72(m, 2H), 2.47(m, 2H), 2.31-2.00(m, 5H), 1.66-1.52(m, 8H).

Example 5 cis-1-[2-(2-Acetyl-octahydro-cyclopenta[c]pyrrol-5-ylamino)-acetyl]-pyrrolidine-2-carbonitrile

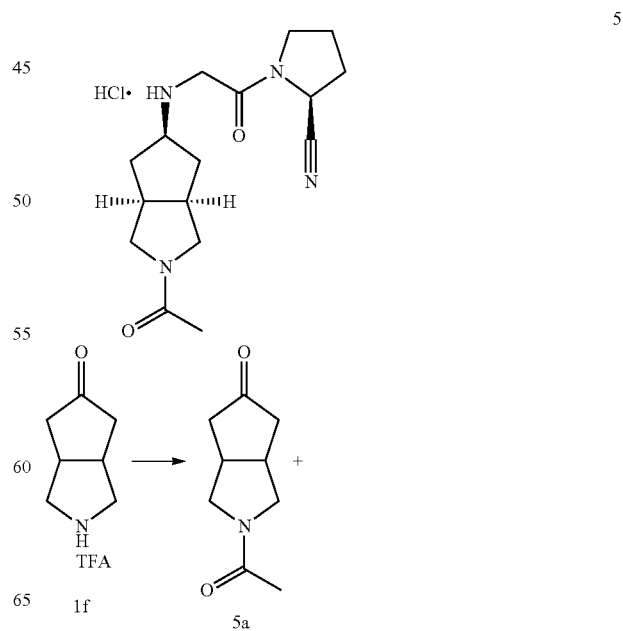

5

1f     5a

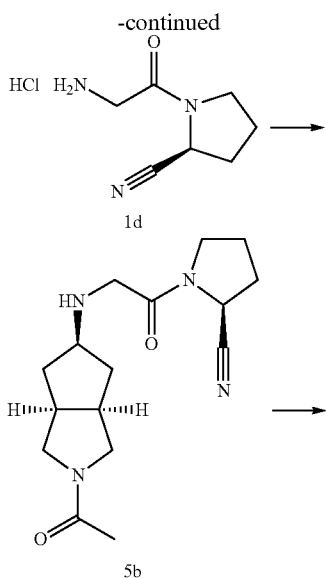

5b

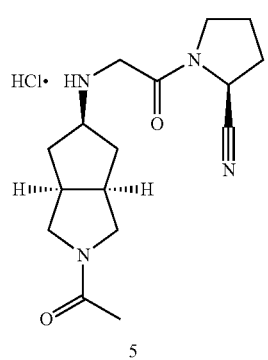

5

Preparation of 2-acetyl-hexahydro-cyclopenta[c]pyrrol-5-one 5a

Hexahydro-cyclopenta[c]pyrrol-5-one triflutate 1f (717 mg, 3 mmol) was dissolved in 20 mL of acetonitrile, and acetic anhydride (0.42 mL, 4.5 mmol) and triethylamine (0.98 mL, 9 mmol) were then added to the solution in an ice-water bath. Upon completion of the addition, the reaction mixture was then stirred overnight in an ice-water bath. The solvent was evaporated, and water (50 mL) was then added to the residue. The mixture was extracted with ethyl acetate (50 mL×3). The combined organic extracts were washed with 50 mL of saturated brine, dried over anhydrous magnesium sulfate, filtered and concentrated under reduced pressure. The residue was purified by silica gel column chromatography to obtain the title compound 2-acetyl-hexahydro-cyclopenta[c]pyrrol-5-one 5a (0.36 g, yield 72%) as a colorless oil.

MS m/z (ESI): 168.4(M+1)

Preparation of cis-1-[2-(2-acetyl-octahydro-cyclopenta[c]pyrrol-5-ylamino)-acetyl]-pyrrolidine-2-carbonitrile 5b 2-Acetyl-hexahydro-cyclopenta[c]pyrrol-5-one 5a (0.36 g, 2.15 mmol) and 1-(2-amino-acetyl)-pyrrolidine-2-carbonitrile hydrochloride 1d (0.614 g, 3.23 mmol) were dissolved in 50 mL of tetrahydrofuran, and sodium sulfate (5 g) and acetic acid (0.05 mL) were then added to the solution. Upon completion of the addition, the reaction mixture was stirred for 0.5 hour at room temperature, sodium triacetoxyborohydride (1.37 g, 6.46 mmol) was then added to the mixture, and the mixture was stirred for 3 hours at room temperature. The reaction mixture was concentrated under reduced pressure, and saturated sodium carbonate solution (50 mL) was then added to the mixture. The reaction mixture was extracted with ethyl acetate (50 mL×3). The combined organic extracts were washed with 50 mL of saturated brine and 50 mL of water successively, dried over anhydrous magnesium sulfate, filtered and concentrated under reduced pressure. The residue was purified by silica gel column chromatography to obtain the title compound cis-1-[2-(2-acetyl-octahydro-cyclopenta[c]pyrrol-5-ylamino)-acetyl]-pyrrolidine-2-carbonitrile 5b which was directly used in the further reaction.

MS m/z (ESI): 305.5(M+1)

Preparation of cis-1-[2-(2-acetyl-octahydro-cyclopenta[c]pyrrol-5-ylamino)-acetyl]-pyrrolidine-2-carbonitrile hydrochloride 5

The resulting cis-1-[2-(2-Acetyl-octahydro-cyclopenta[c]pyrrol-5-ylamino)-acetyl]-pyrrolidine-2-carbonitrile 5b was dispersed in 20 mL of ether, and a solution of 0.5 N hydrochloride acid in 4 mL of ether was then added to the solution in an ice-water bath. The precipitate was centrifuged to obtain the title compound cis-1-[2-(2-acetyl-octahydro-cyclopenta[c]pyrrol-5-ylamino)-acetyl]-pyrrolidine-2-carbonitrile hydrochloride 5 (0.23 g) as a white powder.

$^1$H NMR (CD$_3$OD, 400 MHz) δ 4.71(m, 1H), 3.92(m, 2H), 3.69-3.37(m, 7H), 2.69(m, 2H), 2.33(m, 2H), 2.13(m, 2H), 2.04-2.00(m, 5H), 1.48(m, 2H).

Example 6 cis-5-[2-(2-Cyano-pyrrolidin-1-yl)-2-oxo-ethylamino]-hexahydro-cyclopenta[c]pyrrole-2-carboxylic acid isopropylamide hydrochloride

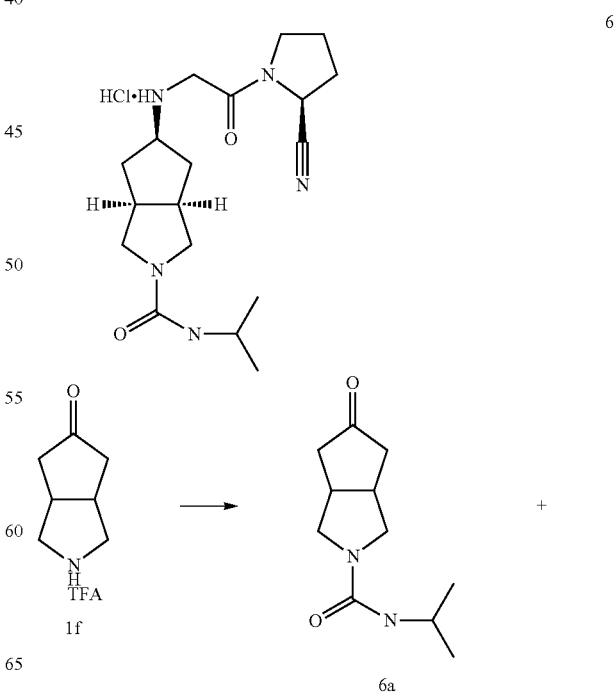

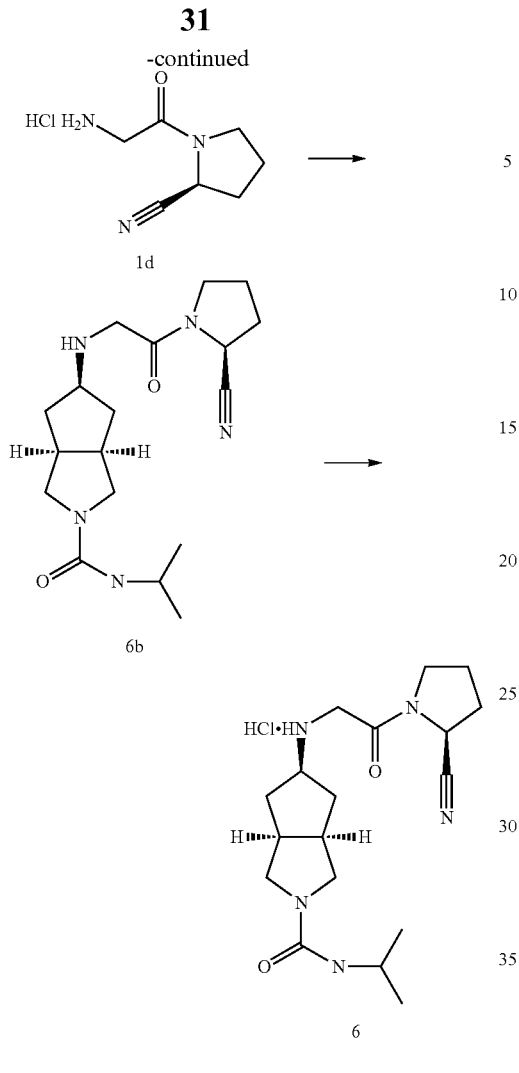

Preparation of 5-oxo-hexahydro-cyclopenta[c]pyrrole-2-carboxylic acid isopropylamide 6a Hexahydro-cyclopenta[c]pyrrol-5-one triflutate 1f (717 mg, 3 mmol) was dissolved in 20 mL of dichloromethane, and 2-isocyanatopropane (9 mL, 9 mmol) and triethylamine (1.7 mL, 12 mmol) were then added to the solution in an ice-water bath. Upon completion of the addition, the reaction mixture was stirred overnight at room temperature, water (50 mL) was then added to the mixture. The mixture was extracted with dichloromethane (50 mL×3). The combined organic extracts were washed with 10% citric acid solution (50 mL) and 50 mL of saturated brine successively, dried over anhydrous magnesium sulfate, filtered and concentrated under reduced pressure. The residue was purified by silica gel column chromatography to obtain the title compound 5-oxo-hexahydro-cyclopenta[c]pyrrole-2-carboxylic acid isopropylamide 6a (0.3 g, yield 47.6%) as a colorless oil.

MS m/z (ESI): 211(M+1)

Preparation of cis-5-[2-(2-cyano-pyrrolidin-1-yl)-2-oxo-ethylamino]-hexahydro-cyclopenta[c]pyrrole-2-carboxylic acid isopropylamide 6b 5-Oxo-hexahydro-cyclopenta[c]pyrrole-2-carboxylic acid isopropylamide 6a (0.3 g, 1.43 mmol) and (s)-1-(2-amino-acetyl)-pyrrolidine-2-carbonitrile hydrochloride 1d (0.407 g, 2.14 mmol) were dissolved in 50 mL of tetrahydrofuran, and sodium sulfate (5 g) and acetic acid (0.05 mL) were then added to the solution. Upon completion of the addition, the reaction mixture was stirred for 0.5 hour at room temperature, sodium triacetoxyborohydride (0.9 g, 4.3 mmol) was then added to the mixture, and the mixture was stirred for 3 hours at room temperature. The reaction mixture was concentrated under reduced pressure, and saturated sodium carbonate solution (50 mL) was then added to the mixture. The reaction mixture was extracted with ethyl acetate (50 mL×3). The combined organic extracts were washed with 50 mL of saturated brine and 50 mL of water successively, dried over anhydrous magnesium sulfate, filtered and concentrated under reduced pressure. The residue was purified by silica gel column chromatography to obtain the title compound cis-5-[2-(2-cyano-pyrrolidin-1-yl)-2-oxo-ethylamino]-hexahydro-cyclopenta[c]pyrrole-2-carboxylic acid isopropylamide 6b which was directly used in the further reaction.

MS m/z (ESI): 384(M+1)

Preparation of cis-5-[2-(2-cyano-pyrrolidin-1-yl)-2-oxo-ethylamino]-hexahydro-cyclopenta[c]pyrrole-2-carboxylic acid isopropylamide hydrochloride 6

The resulting cis-5-[2-(2-cyano-pyrrolidin-1-yl)-2-oxo-ethylamino]-hexahydro-cyclopenta[c]pyrrole-2-carboxylic acid isopropylamide 6b was dispersed in 10 mL of ether, and a solution of 0.5 N hydrochloride acid in 2 mL of ether was then added to the solution in an ice-water bath. The precipitate was centrifuged to obtain the title compound cis-5-[2-(2-cyano-pyrrolidin-1-yl)-2-oxo-ethylamino]-hexahydro-cyclopenta[c]pyrrole-2-carboxylic acid isopropylamide hydrochloride 6 (80 mg) as a white powder.

$^1$H NMR (CD$_3$OD, 400 MHz) δ 4.70(m, 1H), 3.92(m, 2H), 3.76-3.32(m, 8H), 2.63-1.41(m, 10H), 1.01(d, 6H, J=6 Hz).

Example 7 cis-1-{2-[2-(Morpholine-4-carbonyl)-octahydro-cyclopenta[c]pyrrol-5-ylamino]-acetyl}-pyrrolidine-2-carbonitrile hydrochloride

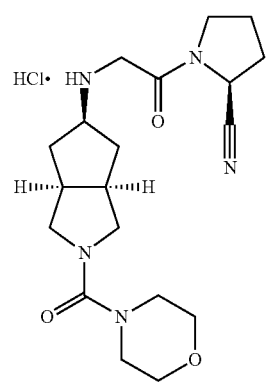

7

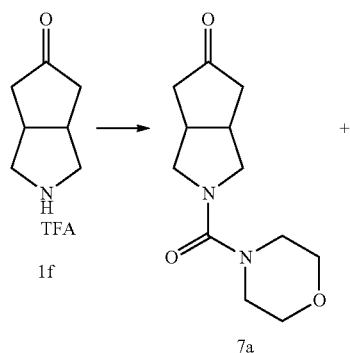

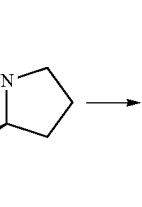

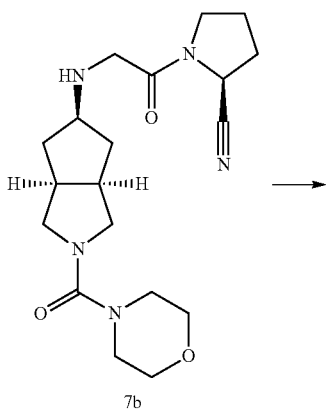

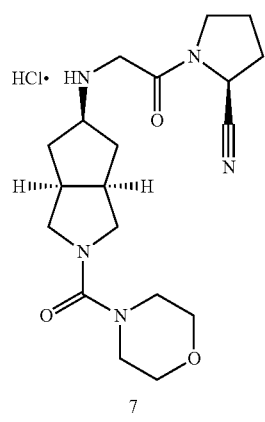

Preparation of 2-(morpholine-4-carbonyl)-hexahydro-cyclopenta[c]pyrrol-5-one 7a

Hexahydro-cyclopenta[c]pyrrol-5-one triflutate 1f (574 mg, 2.4 mmol) was dissolved in 20 mL of acetonitrile with stirring, and potassium carbonate (0.397 g, 2.88 mmol) was then added to the solution in an ice-water bath, followed by morpholine-4-carbonyl chloride (0.323 mL, 2.64 mmol). Upon completion of the addition, the reaction mixture was stirred overnight in an ice-water bath, then the solvent was evaporated, and water (50 mL) was added to the residue. The mixture was extracted with ethyl acetate (50 mL×3). The combined organic extracts were washed with 50 mL of saturated brine, dried over anhydrous magnesium sulfate, filtered and concentrated under reduced pressure. The residue was purified by silica gel column chromatography to obtain the title compound 2-(morpholine-4-carbonyl)-hexahydro-cyclopenta[c]pyrrol-5-one 7a (0.572 g, yield 77.3%) as a colorless oil.

MS m/z (ESI): 239(M+1)

Preparation of cis-1-{2-[2-(morpholine-4-carbonyl)-octahydro-cyclopenta[c]pyrrol-5-ylamino]-acetyl}-pyrrolidine-2-carbonitrile 7b 2-(Morpholine-4-carbonyl)-hexahydro-cyclopenta[c]pyrrol-5-one 7a (0.64 g, 2.69 mmol) and 1-(2-amino-acetyl)-pyrrolidine-2-carbonitrile hydrochloride 1d (0.764 g, 4.03 mmol) were dissolved in 50 mL of tetrahydrofuran, and sodium sulfate (5 g) and acetic acid (0.05 mL) were then added to the solution. Upon completion of the addition, the reaction mixture was stirred for 0.5 hour at room temperature, sodium triacetoxyborohydride (1.71 g, 8.07 mmol) was then added to the mixture, and the mixture was stirred for 3 hours at room temperature. The reaction mixture was concentrated under reduced pressure, and saturated sodium carbonate solution (50 mL) was then added to the residue. The reaction mixture was extracted with ethyl acetate (50 mL×3). The combined organic extracts were washed with 50 mL of saturated brine and 50 mL of water successively, dried over anhydrous magnesium sulfate, filtered and concentrated under reduced pressure. The residue was purify by silica gel column chromatography to obtain the title compound cis-1-{2-[2-(morpholine-4-carbonyl)-octahydro-cyclopenta[c]pyrrol-5-ylamino]-acetyl}-pyrrolidine-2-carbonitrile 7b to be used in the further reaction.

MS m/z (ESI): 376.7(M+1)

Preparation of cis-1-{2-[2-(morpholine-4-carbonyl)-octahydro-cyclopenta[c]pyrrol-5-ylamino]-acetyl}-pyrrolidine-2-carbonitrile hydrochloride 7

The resulting cis-1-{2-[2-(morpholine-4-carbonyl)-octahydro-cyclopenta[c]-pyrrol-5-ylamino]-acetyl}-pyrrolidine-2-carbonitrile 7b was dispersed in 10 mL of ether, and a solution of 0.5 N hydrochloride acid in 2 mL of ether was then added to the solution in an ice-water bath. The precipitate was centrifuged to obtain the title compound cis-1-{2-[2-(morpholine-4-carbonyl)-octahydro-cyclopenta[c]pyrrol-5- ylamino]-acetyl}-pyrrolidine-2-carbonitrile hydrochloride 7 (30 mg, yield 3%) as a white powder.

Example 8 cis-1-{2-[2-(Pyrrolidine-1-carbonyl)-octahydro-cyclopenta[c]pyrrol-5-ylamino]-acetyl}-pyrrolidine-2-carbonitrile hydrochloride

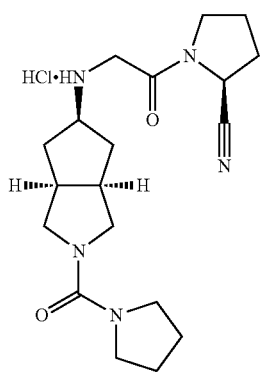

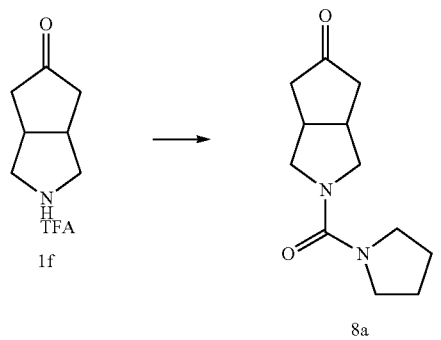

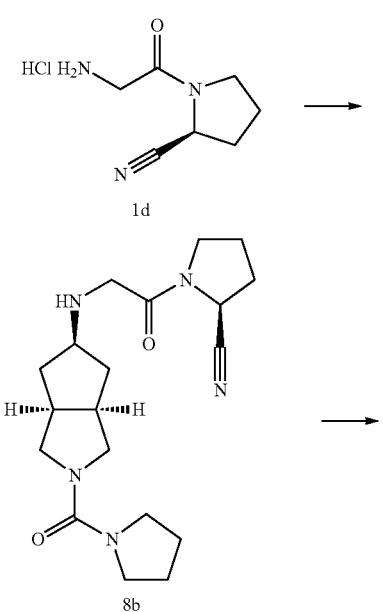

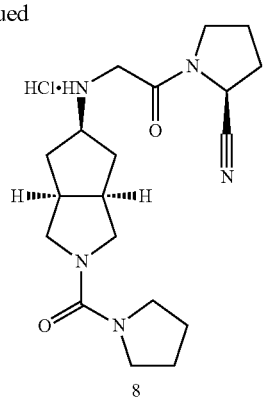

Preparation of 2-(pyrrolidine-1-carbonyl)-hexahydro-cyclopenta[c]pyrrol-5-one 8a Hexahydro-cyclopenta[c]pyrrol-5-one triflutate 1f (478 mg, 2 mmol) was dissolved in 20 mL dichloromethane, and pyrrolidine-1-carbonyl chloride (0.276 mL, 2.5 mmol) and triethylamine (0.84 mL, 6 mmol) were then added to the solution in an ice-water bath. Upon completion of the addition, the reaction mixture was stirred overnight at room temperature, 10% citric acid solution was then added to the mixture to adjust to pH 4. The mixture was extracted with dichloromethane (50 mL×3). The combined organic extracts were washed with 50 mL of saturated brine, dried over anhydrous magnesium sulfate, filtered and concentrated under reduced pressure. The residue was purified by silica gel column chromatography to obtain the title compound 2-(pyrrolidine-1-carbonyl)-hexahydro-cyclopenta[c]pyrrol-5-one 8a (0.26 g, yield 58.5%) as a colorless oil.

MS m/z (ESI): 223(M+1)

Preparation of cis-1-{2-[2-(pyrrolidine-1-carbonyl)-octahydro-cyclopenta[c]pyrrol-5-ylamino]-acetyl}-pyrrolidine-2-carbonitrile 8b 2-(Pyrrolidine-1-carbonyl)-hexahydro-cyclopenta[c]pyrrol-5-one 8a (0.26 g, 1.17 mmol) and 1-(2-amino-acetyl)-pyrrolidine-2-carbonitrile hydrochloride 1d (0.33 g, 1.75 mmol) were dissolved in 50 mL of tetrahydrofuran, and sodium sulfate (5 g) and acetic acid (0.05 mL) were then added to the solution. Upon completion of the addition, the reaction mixture was stirred for 0.5 hour at room temperature, sodium triacetoxyborohydride (0.75 g, 3.5 mmol) was then added to the mixture, and the mixture was stirred for 3 hours at room temperature. The reaction mixture was concentrated under reduced pressure, and saturated sodium carbonate solution (50 mL) was then added to the mixture. The reaction mixture was extracted with ethyl acetate (50 mL×3). The combined organic extracts were washed with 50 mL of saturated brine and 50 mL of water, dried over anhydrous magnesium sulfate, filtered and concentrated under reduced pressure. The residue was purified by silica gel column chromatography to obtain the title compound cis-1-{2-[2-(pyrrolidine-1-carbonyl)-octahydro-cyclopenta[c]pyrrol-5-ylamino]-acetyl}-pyrrolidine-2-carbonitrile 8b which was directly used in the further reaction.

MS m/z (ESI): 396(M+1)

Preparation of cis-1-{2-[2-(pyrrolidine-1-carbonyl)-octahydro-cyclopenta[c]pyrrol-5-ylamino]-acetyl}-pyrrolidine-2-carbonitrile hydrochloride 8

The resulting cis-1-{2-[2-(pyrrolidine-1-carbonyl)-octahydro-cyclopenta[c]pyrrol-5-ylamino]-acetyl}-pyrrolidine-2-carbonitrile 8b was dispersed in 10 mL of ether, and a solution of 0.5 N hydrochloride acid in 2 mL of ether was then added to the solution in an ice-water bath. The precipitate was centrifuged to obtain the title compound cis-1-{2-[2-(pyrrolidine-1-carbonyl)-octahydro-cyclopenta[c]pyrrol-5-ylamino]-acetyl}-pyrrolidine-2-carbonitrile hydrochloride 8 (90 mg) as a white powder.

$^1$H NMR (CD$_3$OD, 400 MHz) δ 4.72(m, 1H), 4.09(m, 2H), 3.43-3.30(m, 11H), 2.62(m, 2H), 2.35(m, 2H), 2.18(m, 2H), 2.08(m, 2H), 1.77(m, 4H)

Example 9 cis-5-[2-(2-Cyano-pyrrolidin-1-yl)-2-oxo-ethylamino]-hexahydro-cyclopenta[c]pyrrole-2-carboxylic acid dimethylamide triflutate

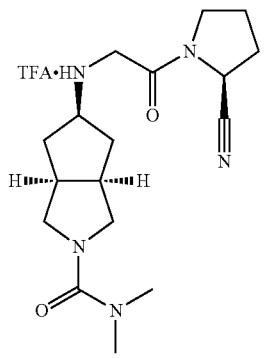

The resulting cis-5-[2-(2-cyano-pyrrolidin-1-yl)-2-oxo-ethylamino]-hexahydro-cyclopenta[c]pyrrole-2-carboxylic acid dimethylamide 1h (157 mg, 0.54 mmol) from example 1 was dispersed in 10 mL of dichloromethane, and trifluoroacetic acid (2 mL) was then added to the solution in an ice-water bath. The reaction mixture was stirred for 0.5 hour. The precipitate was centrifuged to obtain the title compound cis-5-[2-(2-cyano-pyrrolidin-1-yl)-2-oxo-ethylamino]-hexahydro-cyclopenta[c]pyrrole-2-carboxylic acid dimethylamide triflutate 9 (201 mg) as a white powder.

$^1$H NMR (CDCl$_3$, 400 MHz) δ 4.74(t, 1H, J=5.2 Hz), 3.98(d, 1H, J=15.6 Hz), 3.79(d, 1H, J=15.6 Hz), 3.57-3.25(m, 7H), 2.75(s, 6H), 2.55(m, 2H), 2.33(m, 2H), 2.20-2.08(m, 4H), 1.74(m, 2H)

Example 10 trans-5-[2-(2-Cyano-pyrrolidin-1-yl)-2-oxo-ethylamino]-hexahydro-cyclopenta[c]pyrrolo-2-carboxylic acid dimethylamide triflutate

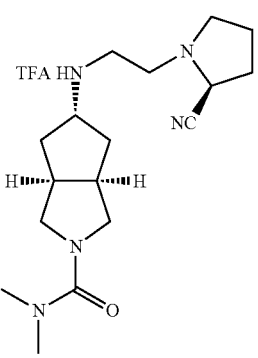

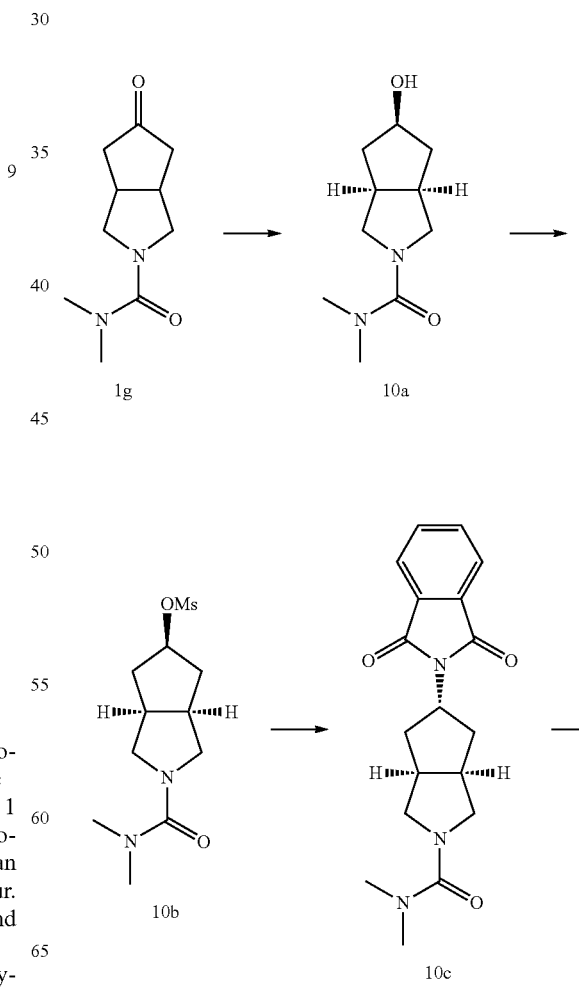

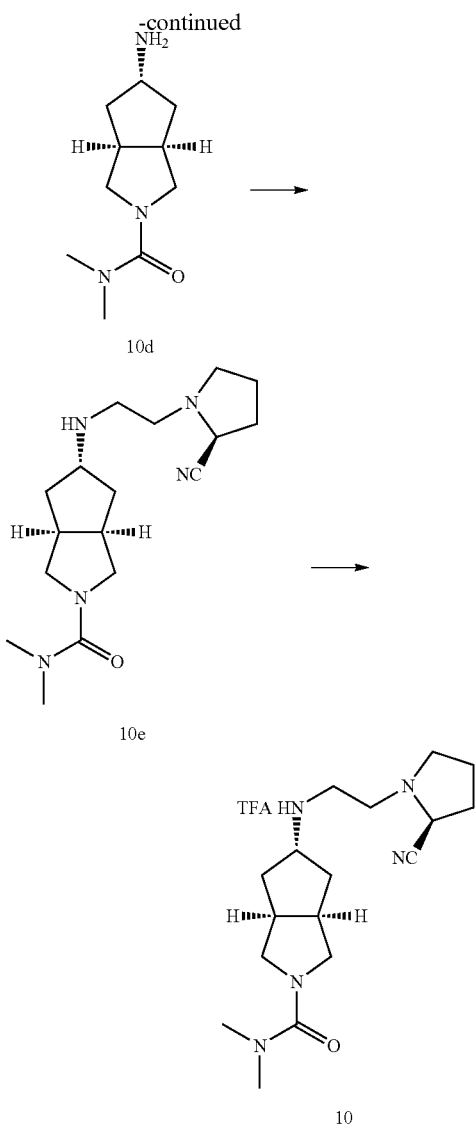

Preparation of cis-5-hydroxy-hexahydro-cyclopenta[c]pyrrole-2-carboxylic acid dimethylamide 10a In a dry three-neck flask under a nitrogen atmosphere, 5-oxo-hexahydro-cyclopenta[c]pyrrole-2-carboxylic acid dimethylamide 1g (1.58 g, 8.06 mmol) was dissolved in 30 mL of tetrahydrofuran, and a solution of lithium tri-tert-butoxyaluminium hydride (2.45 g, 9.6 mmol) in 30 mL of tetrahydrofuran was then added dropwise at −25° C. with stirring. Upon completion of the addition, the reaction mixture was stirred for 2.5 hours at −25° C., and water was added to quench the reaction. 20 mL of saturated ammonium chloride was added to the mixture, then the reaction mixture was allowed to increase to room temperature, and extracted with dichloromethane (50mL×3). The combined organic extracts were washed with 50 mL of saturated brine, dried over anhydrous magnesium sulfate, filtered and concentrated under reduced pressure. The residue was purified by silica gel column chromatography to obtain the title compound cis-5-hydroxy-hexahydro-cyclopenta[c]pyrrole-2-carboxylic acid dimethylamide 10a (1.27 g, yield 80%) as a colorless oil.

MS(m/z) (ESI): 199(M+1)

Preparation of cis-methanesulfonic acid 2-dimethyl-carbamoyl-octahydro-cyclopenta[c]pyrrol-5-yl ester 10b In a dry one-neck flask under a nitrogen atmosphere, cis-5-hydroxy-hexahydro-cyclopenta[c]pyrrole-2-carboxylic acid dimethylamide 10a (1.69 g, 8.5 mmol) was dissolved in 30 mL of dichloromethane, and triethylamine (1.66 mL, 14.45 mmol) and methanesulfonyl chloride (2.2 g, 21.74 mmol) were then added successively in an ice-water bath. The reaction mixture was stirred for 0.5 hour, and allowed to increase to room temperature, then the reaction mixture was stirred for 2 hours, concentrated under reduced pressure, and water (20 mL) was added to the mixture. The reaction mixture was extracted with ethyl acetate (50 mL×6). The combined organic extracts were washed with 50 mL of saturated brine, dried over anhydrous magnesium sulfate, filtered and concentrated under reduced pressure. The residue was purified by silica gel column chromatography to obtain the title compound cis-methanesulfonic acid 2-dimethylcarbamoyl-octahydro-cyclopenta[c]pyrrol-5-yl ester 10b (1.94 g, yield 83%) as a wliite powder.

MS(m/z)(ESI): 277(M+1)

Preparation of trans-5-(1,3-dioxo-1,3-dihydro-isoindol-2-yl)-hexahydro-cyclopenta[c]pyrrole-2-carboxylic acid dimethylamide 10c In a dry one-neck flask under a nitrogen atmosphere, cis-methanesulfonic acid 2-dimethylcarbamoyl-octahydro-cyclopenta[c]pyrrol-5-yl ester 10b (1 g, 3.6 mmol) was dissolved in 20 mL of N,N-dimethylformamide, and phthalimide potassium salt (993 mg, 5.4 mmol) was then added to the solution. Upon completion of the addition, the reaction mixture was allowed to increase to 70° C., and stirred for 3 hours. The mixture was concentrate under reduced pressure, and water (20 mL) was added to the mixture. The reaction mixture was extracted with ethyl acetate (50 mL×3). The combined organic extracts were washed with 50 mL of saturated brine, dried over anhydrous magnesium sulfate, filtered and concentrated under reduced pressure. The residue was purified by silica gel column chromatography to obtain the title compound trans-5-(1,3-dioxo-1,3-dihydro-isoindol-2-yl)-hexahydro-cyclopenta[c]pyrrole-2-carboxylic acid dimethylamide 10c (1.06 g, yield 90%) as a white powder which was directly used in the further reaction.

MS(m/z)(ESI): 328(M+1)

Preparation of trans-5-amino-hexahydro-cyclopenta[c]pyrrole-2-carboxylic acid dimethylamide 10d In a one-neck flask, trans-5-(1,3-dioxo-1,3-dihydro-isoindol-2-yl)-hexahydro-cyclopenta[c]pyrrole-2-carboxylic acid dimethylamide 10c (1 g, 3.06 mmol) was dissolved in 20 mL of 95% ethanol, and hydrazine (490 mg, 15.3 mmol) was then added to the solution. Upon completion of the addition, the reaction mixture was heated to reflux for 8 hours, cooled down to room temperature, filtered and the filtrate was concentrated tinder reduced pressure to obtain a white powder. Methanol (25 mL) was added, and the resulting mixture was filtered and concentrated under reduced pressure. The residue was purified by Basic alumina column chromatography to obtain trans-5-amino-hexahydro-cyclopenta[c]pyrrole-2-carboxylic acid dimethylamide 10d (290 mg, yield 48%) as a colorless oil.

MS(m/z)(ESI): 198(M+1)

Preparation of trans-5-[2-(2-cyano-pyrrolidin-1-yl)-2-oxo-ethylamino]-hexahydro-cyclopenta[c]pyrrole-2-carboxylic acid dimethylamide triflutate 10

In a one-neck flask, trans-1-(2-chloro-ethyl)-pyrrolidine-2-carbonitrile (334 mg, 1.94 mmol) was added, followed by a solution of 5-amino-hexahydro-cyclopenta[c]pyrrole-2-carboxylic acid dimethylamide 10d (290 mg, 1.46 mmol) in 20 mL of dichloromethane. Upon completion of the addition, the reaction mixture was heated to reflux for 48 hours, concentrated under reduced pressure. The residue was purified by silica gel column chromatography to obtain trans-5-[2-(2-cyano-pyrrolidin-1-yl)-2-oxo-ethylamino]-hexahydro-cyclopenta[c]pyrrole-2-carboxylic acid dimethylamide 10e. Then, trans-5-[2-(2-cyano-pyrrolidin-1-yl)-2-oxo-ethylamino]-hexahydro-cyclopenta[c]pyrrole-2-carboxylic acid dimethylamide 10e was dissolved in 10 mL of dichloromethane with stirring, and trifluoroacetic acid (2 mL) was then added to the solution in an ice-water bath. The reaction mixture was stirred for 0.5 hour to obtain the title compound trans-5-[2-(2-cyano-pyrrolidin-1-yl)-2-oxo-ethylamino]-hexahydro-cyclopenta[c]pyrrole-2-carboxylic acid dimethylamide triflutate 10 (201 mg) as a white solid.

MS(m/z)(ESI): 334(M+1)

$^1$H EVER (CDCl$_3$, 400 MHz) δ 465(m, 1H) 3.93(d, 1H, J=15.2 Hz), 3.74(d, 1H, J=15.2 Hz), 3.69-3.19(m, 7H), 2.77 (s, 6H), 2.18-1.96(m, 10H).

Biological Assays

Active Inhibition DPP IV Assay

Assay Procedures

The following methods can be used to measure the activities of the compounds of the invention which inhibit the enzymatic activity of DPP-IV. The compounds of the invention are tested for their ability to inhibit the enzyme activity of purified DPP-IV. The inhibition rates or the IC$_{50}$ (concentration of test compound at which 50% of the enzyme activity is inhibited) for each compound is determined by incubating fixed amounts of enzyme mixed substrate with several different concentrations of tested compounds.

Materials and Methods:

Materials include:
  a. White 96-well plates (BMG),
  b. Tris Buffer, to prepare 100 ml 2 mM Tris Buffer in dH$_2$O, 0.0242 g Tris was dissolved in approx. 90 ml dH$_2$O and pH was adjusted with HCl and NaOH to 8.00, at least dH$_2$O was added to 100 ml,
  c. DPPIV enzyme (CalBiochem Catalog no. 317630), dissolved in Tris Buffer to 2 mM,
  d. DPPIV-Glo™ Subtrate (Promega Catalog no. G8350), dissolved in dH$_2$O to 1 mM,
  e. DPPIV-Glo. Buffer (Promega Catalog no. G8350),
  f. Luciferin Detection Reagent (Promega Catalog no. G8350),
  g. DMSO, and
  h. dH$_2$O.

Protocol:

The assay was carried out in the order of the following steps of:

1. Thawing the DPPIV-Glo. Buffering and equilibrating it to room temperature prior to use;
2. Equilibrating the lyophilized Luciferin Detection Reagent to room temperature prior to use;
3. Suspending the DPPIV-Glo., adding ultrapure water to the substrate vial to mix briefly, then giving 1 mM substrate;
4. Adding the Luciferin Detection Reagent to the amber bottle, followed by DPPIV-Glo. Buffer, wherein the Luciferin Detection Reagent should be dissolved in less than one minute;
5. Dissolving a tested compound to 50 fold of the desired final concentration with DMSO;
6. Adding 2 μL tested compound with a 50 fold concentration to each tube, adding 2 μL DMSO in negative and blank controls;
7. Adding 46 μL Tris Buffer to each tube, adding 48 μL Tris Buffer in blank controls;
8. Addind 2 μL DPPIV enzyme to each tube for negative controls and tested compounds;
9. Swirling and centrifuging the tubes, then transferring the substances of the tubes to the 96-well plate;
10. Mixing Substrate and DPPIV-Gloat the rate 1:49, then swirling or inverting the substances to obtain a homogeneous solution, and standing it at room temperature for 30-60 minutes prior to use;
11. Adding 50 μL of the mixed solution of DPPIV-Glo. and substrate to each 96-well plate, and covering the plate with a sealing film;
12. Gently mixing the substances of the 96 wells using a plate shaker at 300-500 rpm for 30 seconds, then incubating them at room temperature for 30 minutes to 3 hours; and
13. Recording luminescence.

The inhibition rate can be defined as: [1−(S−B)/(N−B)]*100%

S: sample
B: blank control
N: negative control

IC$_{50}$ of the DPP IV of the tested compounds were showed in table 1:

TABLE 1

| IC$_{50}$ assay results of examples | |
|---|---|
| examples | IC$_{50}$(DPPIV)/nM |
| 1 | 9 |
| 2 | 24 |
| 3 | 14 |
| 4 | 69 |
| 7 | 50 |
| 8 | 39 |

The Selective Activity Determination of DPPIV Inhibitors

Objective:

Human DPPIV (EC 3.14.21.5; Depeptidyl peptidase IV; T cell activated antigen CD26; ADA binding protein) has the activity of dipeptide aminopeptidase. It can cut off the first two amino acids in many of the N-peptide to change or lose its biological activity. Gene knockout animal and human experiments indicate that reducing DPPIV activity effectively and specifically in vivo can improve blood insulin content and lower blood sugar levels, so as to improve the symptoms of diabetes effectively. Recent studies show that there are a number of proteins (DASH) as same as DPPIV protein in activity and structure, including DPP8, DPP9, QPP and FAP and the like. Pre-clinical studies show that inhibiting the activities of these DASH members will lead to toxicity, even death. Therefore, screening DPPIV inhibitors with high selectivity and efficient has an important value for the treatment of diabetes.

Methods:

By using the insect expression system, the recombinant proteins of DPPIV, DPP8, DPP9 and QPP had been obtained. The activities of the five enzymes were detected by fluorescence Substrate. The inhibitory effects of compounds were evaluated by the effects of different compounds on inhibiting enzyme activities. Positive reference compound was LAF237.

Results:

The IC50s of Compounds:

| Example | IC50 (nM) DPPIV | IC50 (nM) DPP8 | IC50 (nM) DPP9 | IC50 (nM) QPP | IC50 (nM) FAP |
|---------|-----------------|----------------|----------------|---------------|---------------|
| 1 | 16.2 ± 5.1 | 17381 ± 4947 | 5703.6 ± 162.2 | >54062.8 | 540.6 ± 54.0 |
| 2 | 98.0 ± 36.4 | 18241 ± 2690 | 5043.6 ± 560.4 | >56039.7 | 476.3 ± 112.1 |

Conclusion:
The two compounds can inhibit DPPIV activity obviously, have the significant selectivity on QPP and have different degree selectivity on DPP8, DPP9 and FAP.

Preliminary Evaluation of Hypoglycemic Effects of DPPIV Inhibitors

Objective:

To observe the effects on oral glucose tolerance of the DPPIV inhibitors SHR1039 (example 1) and SHR1040 (example 2) in normal ICR mice, the hypoglycemic effects in vivo have been evaluated.

Test Animals:

| | |
|---|---|
| Species, strains: | ICR mice |
| Source: | Chinese Academy of Sciences, Shanghai Laboratory Animal Center, Qualified No.: SYXK (Shanghai) 2004-2005 |
| Weight: | 25-30 g |
| Sex: | Male animals |
| Animal Number: | 40 |
| Rearing conditions: | SPF-class animal room raising, temperature: 22-24° C., Humidity: 45-80%, illumination: 150-300Lx, day and night cycle with an interval of 12 hours. |

Drugs:

| | |
|---|---|
| Name: | SHR1039 (Example 1) |
| Lot Number: | 01 |
| Color, form: | white powder |
| Purity: | 96.97% |
| Provided by: | Shanghai Hengrui Medicine Co., Ltd. |
| Preparation Method: | Compounds were weighed accurately, and then dissolved in double distilled water. The suspensions of 0.5, 0.15 and 0.05 mg/ml were prepared respectively. (Note: Although the product instruction displayed the test compounds were soluble in water, but in the experiment it was poor water-soluble, i.e., at low concentration it can be dissolved, but at the concentration of 0.5 mg/ml there are still visible particles by the naked eye. 1% CMC was tried to suspend the compounds, while it was not better than double-distilled water.) |
| Dose: | 1, 3, 10 mg/kg by gavage. The volume is 20 ml/kg. |
| Name: | SHR1040 (Example 2) |
| Lot Number: | 01 |
| Color, form: | white powder |
| Purity: | 96.62% |
| Provided by: | Shanghai Hengrui Medicine Co., Ltd. |
| Preparation Method: | Compounds were weighed accurately, and then dissolved in double distilled water and fully mixed to prepare a 1.5 mg/ml solution, and then diluted into 0.5, 0.15 and 0.05 mg/ml transparent solution respectively. |
| Dose: | 1, 3, 10 mg/kg by gavage. The volume is 20 ml/kg. |

Method:

1. The Effects of Compounds on Blood Glucose in Normal ICR Mice

Normal male ICR mice were randomly grouped according to weights, 6 mice in each group. The groups included a blank control group as well as different doses of the treatment groups as follows:

Test 1:
Blank control: double-distilled water by gavage.
Group 1: SHR1039 (example 1) 1 mg/kg by gavage.
SHR1039 (example 1) 3 mg/kg by gavage.
SHR1039 (example 1) 10 mg/kg by gavage.
Group 2: SHR1040 (example 2) 1 mg/kg by gavage.
SHR1040 (example 2) 3 mg/kg by gavage.
SHR1040 (example 2) 10 mg/kg by gavage.

Test 2:
Blank control: double-distilled water by gavage.
Group 1: SHR1039 (example 1) 1 mg/kg by gavage.
SHR1039 (example 1) 3mg/kg by gavage.
SHR1039 (example 1) 10 mg/kg by gavage.
Group 2: SHR1040 (example 2) 1 mg/kg by gavage.
SHR1040 (example 2) 3 mg/kg by gavage.
SHR1040 (example 2) 10 mg/kg by gavage.

Animals in each group had been fasted for 6 hours, and then pretreated with compounds or double distilled water by gavage respectively in single administration. 30 minutes later, animals were administered 2.5 g/kg glucose by gavage. Before administration and after administration of glucose at 30, 60 and 120 minuets, blood was taken to determine serum glucose levels.

2. Serum Glucose Determination:

Serum glucose is determined by glucose kit. 250 µl working enzyme solution was taken, and then 5 µl serum was added to the solution. A blank tube (5 µl double distilled water was added) and a standard tube (5 µl glucose standard solution was added) were established simultaneously, shaking respectively, and in 37° C. water bath for 20 minutes. The blank tube was tuned with, and then calorimetric assay was determined at OD505 nm.

Serum glucose concentration (BG, mmol/l)=$OD_{sample\ tube}/OD_{standard\ tube} \times 5.55$ Data Processing and Statistical Analysis:

1. Mean±SD and Student-t test were used in data statistical analysis.
2. The percentage of blood glucose decline in 30 minutes after sugar administration as well as the area under the curve (AUC) was calculated.

Results:
Test 1:
Male ICR mice were fasted for 6 hours, and then treated with double distilled water, different doses of tested compounds of example 1 and example 2 by gavage. 30 minutes after administration, the oral glucose tolerance test was made. The results showed that blood glucose level in the control group increased significantly after 2.5 g/kg glucose had administered by gavage, and reached the peak at 30 minutes. At low, middle and high doses of the compound of example 1, blood glucose was significantly lower than control group at 30 minutes, and the percentage of blood glucose thereof had decreased by 19.16%, 22.85 and 31.85% respectively. At each dose of the compound of example 2, blood glucose was significantly lower than control group at 30 minutes after the administration of glucose (P<0.01). Compared with control group, the percentage of blood glucose thereof had decreased by 25.54%, 25.92 and 26.93%.

Test 2:
Male ICR mice were fasted for 6 hours, and then treated with double distilled water; different doses of tested compound SHR1039 (example 1) and SHR1040 (example 2) by gavage. 30 minutes after administration, the oral glucose tolerance test was made. The results showed that blood glucose level in the control group increased significantly after 2.5 g/kg glucose had administered by gavage, and reached the peak at 30 minutes. At each dose of SHR1039, blood glucose was significantly lower than control group at 30 minutes after the administration of glucose (P<0.01), and the percentage of blood glucose thereof had decreased by 26.10%, 30.24 and 32.05% respectively. At low, middle and high doses of SHR1040, blood glucose was significantly lower than control group at 30 minutes (P<0.01), and the percentage of blood glucose thereof had decreased by 24.51%, 26.96% and 27.75%.

Conclusion:
Two experimental results of this report show that tested compounds SHR1039 (example 1), SHR1040 (example 2) have significant hypoglycemic effect on oral glucose tolerance test in normal ICR mice. Moreover, tested compound SHR1039 (example 1) shows a better dose-effect relationship, and test compound SHR1040 (example 2) has a less dose-effect relationship.

Effects of DPPIV Inhibitors on Oral Glucose Tolerance in KKAy Mice

Objective:
To observe the effects of the DPPIV inhibitors SHR1039 (example 1) and SHR1040 (example 2) on oral glucose tolerance in type II diabetes KKAy mice, a preliminary evaluation of their hypoglycemic effect in vivo has been evaluated.

Test Animals:

| | |
|---|---|
| Species, Strains: | KKAy mice |
| Source: | Shanghai Laboratory Animal Center, Chinese Academy of Sciences. Qualified No.: SYXK (Shanghai) 2004-2005 |
| Weight: | 40~55 g |
| Sex: | female: 52; male: 33 |
| Raising Conditions: | SPF grade animal room raising, temperature: 22-24° C.; Humidity: 45-80%; illumination: 150-300Lx, day and night cycle with an interval of 12 hours. |

Drugs:

| | |
|---|---|
| Name: | SHR1039 (example 1) and SHR1040 (example 2) |
| Preparation Method: | Compounds were weighed accurately, then dissolved in double distilled water, and full mixed to prepare a 3 mg/ml suspension, then diluted to 1, 0.3, 0.1 mg/ml transparent solution respectively. |
| Dose: | 1, 3, 10, 30 mg/kg by gavage. The volume is 10 ml/kg. |

Methods:
The effects of the Compounds on Blood Glucose in KKAy Mice
Normal KKAy mice had been fasted for 6 hours, and then were randomly grouped according to weights and fasting blood glucose, 5 mice in each group. The groups included a blank control group as well as different doses of the treatment groups as follows:

| Test 1: male 0704 | |
|---|---|
| Blank control: | double-distilled water by gavage |
| SHR1039: | SHR1039 (example 1) 10 mg/kg by gavage |
| | SHR1039 (example 1) 30 mg/kg by gavage |
| Test 2: female 0816 | |
| Blank control: | double-distilled water by gavage |
| SHR1039: | SHR1039 (example 1) 3 mg/kg by gavage |
| | SHR1039 (example 1) 10 mg/kg by gavage |
| Test 3: male 0712 | |
| Blank control: | double-distilled water by gavage |
| SHR1040: | SHR1040 (example 2) 10 mg/kg by gavage |
| | SHR1040 (example 2) 30 mg/kg by gavage |
| Test 4: female 0907 | |
| Blank control: | double-distilled water by gavage |
| SHR1040: | SHR1040 (example 2) 3 mg/kg by gavage |
| | SHR1040 (example 2) 10 mg/kg by gavage |

Animals in each group had been fasted for 6 hours, and then pretreated with compounds or double distilled water by gavage respectively in single administration. 30 minutes later, animals were administered 2.5 g/kg (female KKAy mice) or 1.5 g/kg (male KKAy mice) glucose by gavage. After administration of glucose at 30, 60 and 120 minuets, serum glucose levels were determined by Glucometer.

Data Processing and Statistical Analysis:
3. Mean±SD and Student-t test or Anova were used in data statistical analysis.
4. The percentage of blood glucose decline in 30 minutes after sugar administration as well as the area under the curve (AUC) was calculated.

Results:
1. Compound SHR1039 (example 1): Test 1, 2
Male KKAy mice were fasted for 6 hours, and then treated with double distilled water and different doses of tested compound SHR1039 (example 1) by gavage. 30 minutes after administration, the oral glucose tolerance test was made. The results showed that the blood glucose level in the control group increased significantly after 1.5 g/kg glucose had administered by gavage, and reached the peak at 30 minutes. In the doses of 10 mg/kg and 30 mg/kg of SHR1039 (example 1) groups, blood glucose levels thereof were both lower than control group at 30 minutes after the administration of glucose. Compared with control group, the percentage of blood glucose thereof had decreased by 16.22% and 17.15% respectively.

Female KKAy mice were fasted for 6 hours, and then treated with double distilled water and different doses of tested compound SHR1039 (example 1) by gavage. 30 minutes after administration, the oral glucose tolerance test was made. The results showed that the blood glucose level in the control group increased significantly after 2.5 g/kg glucose had administered by gavage, and reached the peak at 30 minutes. In the doses of 3 mg/kg and 10 mg/kg of SHR1039 (example 1) groups, blood glucose levels thereof were both significantly lower than control group at 30 minutes after the administration of glucose. The percentage of blood glucose thereof had decreased by 40.63% and 24.68% respectively.

2. Compounds SHR1040 (example 2): Test 3, 4

Male KKAy mice were fasted for 6 hours, and then treated with double distilled water and different doses of tested compound SHR1040 (example 2) by gavage. 30 minutes after administration, the oral glucose tolerance test was made. The results showed that the blood glucose level in the control group increased significantly after 1.5 g/kg glucose had administered by gavage, and reached the peak at 30 minutes. In the doses of 10 mg/kg and 30 mg/kg of SHR1040 (example 2) groups, blood glucose levels thereof were both lower than control group at 30 minutes after the administration of glucose. Compared with control group, the percentage of blood glucose thereof had decreased by 13.79% and 12.23% respectively.

Female KKAy mice were fasted for 6 hours, and then treated with double distilled water and different doses of tested compound SHR1040 (example 2) by gavage. 30 minutes after administration, the oral glucose tolerance test was made. The results showed that the blood glucose level in the control group increased significantly after 2.5 g/kg glucose had administrated by gavage, and reached the peak at 30 minutes. In the dose of 10 mg/kg of SHR1040 (example 2) group, blood glucoses were lower than control group at 30 minutes after the administration of glucose (P=0.075, anova). The percentage of blood glucose thereof had decreased by 21.55%. However, since there is a great individual difference in the mice, the results had no significant difference.

Conclusion:

Tested compounds SHR1039 (example 1) and SHR1040 (example 2) both have some hypoglycemic effects on oral glucose tolerance test in type II diabetes KKAy mice.

What is claimed is:

1. A compound having formula (IA) or a pharmaceutically acceptable salt thereof:

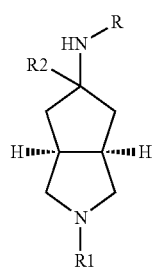

(IA)

wherein R is the following formula:

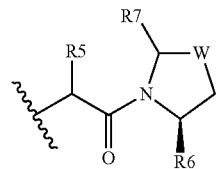

wherein $R_1$ is a member selected from the group consisting of hydrogen, alkyl, cycloalkyl, heterocyclo alkyl, aryl, heteroaryl, —C(O)NR$_3$R$_4$, —C(O)R$_3$ and —C(O)OR$_3$, wherein the alkyl, cycloalkyl, heterocyclo alkyl, aryl or heteroaryl may be substituted with one or more groups selected from the group consisting of alkyl, aryl, hydroxyl, amino, alkoxyl, aryloxyl and heterocyclo alkyl;

$R_2$ is a member selected from the group consisting of hydrogen and methyl;

$R_3$ and $R_4$ are each independently a member selected from the group consisting of hydrogen, alkyl, cycloalkyl, aryl, heteroaryl and heterocycle alkyl, wherein the alkyl, cycloalkyl, aryl, heteroaryl or heterocyclo alkyl may be substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, cyano, hydroxyalkyl, heterocyclo alkyl, heterocyclo alkoxyl, trifluoromethyl, carboxylic acid and carboxylic ester; and $R_3$ and $R_4$ are attached together with the N atom to form a 3 to 8 membered hetero ring, wherein the 3 to 8 membered hetero ring may contain one or more heteroatoms selected from the group consisting of N, O and S atom, and the 3 to 8 membered rings may be substituted with one or more groups selected from the group consisting of alkyl, aryl, heteroaryl, haloalkyl, haloalkoxyl, hydroxyl, amino, cyano, alkoxyl, aryloxyl, hydroxyalkyl, heterocyclo alkyl, carboxylic acid,carboxylic ester, halogen and —NR$_3$R$_4$; and $R_5$ is a member selected from the group consisting of hydrogen, alkyl, cycloalkyl, aryl, heteroaryl and heterocyclo alkyl, wherein the alkyl, cycloalkyl, aryl, heteroaryl or heterocyclo alkyl may be substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, alkylamino, cyano, hydroxyalkyl, heterocyclo alkyl, heterocyclo alkoxyl, carboxylic acid and carboxylic ester;

$R_6$ and $R_7$ are each independently a member selected from the group consisting of alkyl, aryl, heteroaryl, haloalkyl, haloalkoxyl, hydroxyl, amino, cyano, alkynyl, alkoxyl, aryloxyl, hydroxyalkyl, heterocyclo alkyl, carboxylic acid, carboxylic ester and halogen; and W is C.

2. The compound or pharmaceutically acceptable salt thereof of claim 1, wherein the compound has the formula (IB):

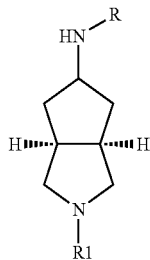

(IB)

wherein R is the following formula:

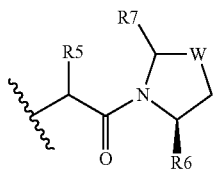

$R_1$ is a member selected from the group consisting of hydrogen, alkyl, cycloalkyl, heterocyclo alkyl, aryl, heteroaryl, —C(O)NR$_3$R$_4$, —C(O)R$_3$ and —C(O)OR$_3$, wherein the alkyl, cycloalkyl, heterocyclo alkyl, aryl or heteroaryl may be substituted with one or more groups selected from the group consisting of alkyl, aryl, hydroxyl, amino, alkoxyl, aryloxyl and heterocyclo alkyl;

$R_3$ and $R_4$ are each independently a member selected from the group consisting of hydrogen, alkyl, cycloalkyl, aryl, heteroaryl and heterocyclo alkyl, wherein the alkyl, cycloalkyl, aryl, heteroaryl or heterocyclo alkyl may be substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, cyano, hydroxyalkyl, heterocyclo alkyl, heterocyclo alkoxyl, trifluoromethyl, carboxylic acid and carboxylic ester; and $R_3$ and $R_4$ are attached together with the N atom to form a 3 to 8 membered hetero ring, wherein the 3 to 8 membered hetero ring may contain one or more heteroatoms selected from the group consisting of N, O and S atom, and the 3 to 8 membered rings may be substituted with one or more groups selected from the group consisting of alkyl, aryl, heteroaryl, haloalkyl, haloalkoxyl, hydroxyl, amino, cyano, alkoxyl, aryloxyl, hydroxyalkyl, heterocyclo alkyl, carboxylic acid, carboxylic ester, halogen and —NR$_3$R$_4$;

$R_5$ is a member selected from the group consisting of hydrogen, alkyl, cycloalkyl, aryl, heteroaryl and heterocyclo alkyl, wherein the alkyl, cycloalkyl, aryl, heteroaryl or heterocyclo alkyl may be substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, alkylamino, cyano, hydroxyalkyl, heterocyclo alkyl, heterocyclo alkoxyl, carboxylic acid and carboxylic ester;

$R_6$ and $R_7$ are each independently a member selected from the group consisting of alkyl, aryl, heteroaryl, haloalkyl, haloalkoxyl, hydroxyl, amino, cyano, alkynyl, alkoxyl, aryloxyl, hydroxyalkyl, heterocyclo alkyl, carboxylic acid, carboxylic ester and halogen; and W is C.

3. The compound or pharmaceutically acceptable salt thereof of claim 1, wherein the compound has the formula (IC):

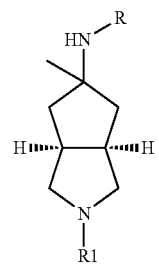

(IC)

wherein R is the following formula:

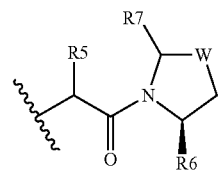

$R_1$ is a member selected from the group consisting of hydrogen, alkyl, cycloalkyl, heterocycle alkyl, aryl, heteroaryl, —C(O)NR$_3$R$_4$, —C(O)R$_3$ and —C(O)OR$_3$, wherein the alkyl, cycloalkyl, heterocyclo alkyl, aryl or heteroaryl may be substituted with one or more groups selected from the group consisting of alkyl, aryl, hydroxyl, amino, alkoxyl, aryloxyl and heterocyclo alkyl;

$R_3$ and $R_4$ are each independently a member selected from the group consisting of hydrogen, alkyl, cycloalkyl, aryl, heteroaryl and heterocyclo alkyl, wherein the alkyl, cycloalkyl, aryl, heteroaryl or heterocyclo alkyl may be substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, cyano, hydroxyalkyl, heterocyclo alkyl, heterocyclo alkoxyl, trifluoromethyl, carboxylic acid and carboxylic ester; and $R_3$ and $R_4$ are attached together with the N atom to form a 3 to 8 membered hetero ring, wherein the 3 to 8 membered hetero ring further contains one or more heteroatoms selected from the group consisting of N, O and S atom, and the 3 to 8 membered rings may be substituted with one or more groups selected from the group consisting of alkyl, aryl, heteroaryl, haloalkyl, haloalkoxyl, hydroxyl, amino, cyano, alkoxyl, aryloxyl, hydroxyalkyl, heterocyclo alkyl, carboxylic acid, carboxylic ester, halogen and —NR$_3$R$_4$;

$R_5$ is a member selected from the group consisting of hydrogen, alkyl, cycloalkyl, aryl, heteroaryl and heterocyclo alkyl, wherein the alkyl, cycloalkyl, aryl, heteroaryl or heterocyclo alkyl may be substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, alkylamino, cyano, hydroxyalkyl, heterocyclo alkyl, heterocyclo alkoxyl, carboxylic acid and carboxylic ester;

$R_6$ and $R_7$ are each independently a member selected from the group consisting of alkyl, aryl, heteroaryl, haloalkyl, haloalkoxyl, hydroxyl, amino, cyano, alkynyl, alkoxyl, aryloxyl, hydroxyalkyl, heterocyclo alkyl, carboxylic acid, carboxylic ester and halogen; and W is C.

4. The compound or pharmaceutically acceptable salt thereof of claim 1, wherein the salt comprises a salt formed with an acid selected from the group consisting of hydrochloric acid, p-toluenesulfonic acid, tartaric acid, maleic acid, lactic acid, methanesulfonic acid, sulfuric acid, phosphoric acid, citric acid, acetic acid and trifluoroacetic acid.

5. The compound or pharmaceutically acceptable salt thereof of claim 4, wherein the acid is p-toluenesulfonic acid, hydrochloric acid or trifluoroacetic acid.

6. The compound or pharmaceutically acceptable salt thereof of claim 1, wherein the compound is one of the following compounds of formulas 1 to 10:

1
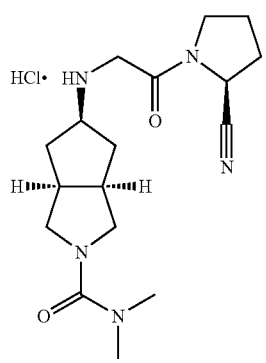

2
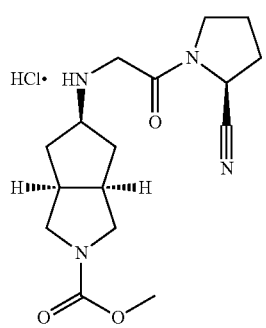

3
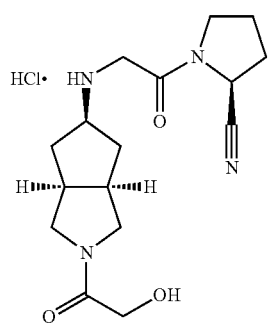

-continued

4
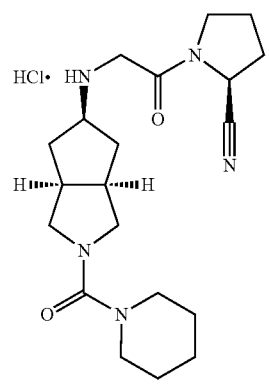

5
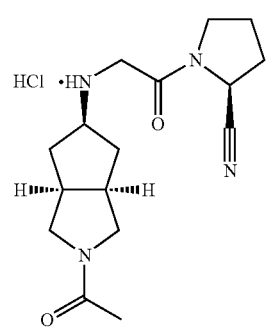

6
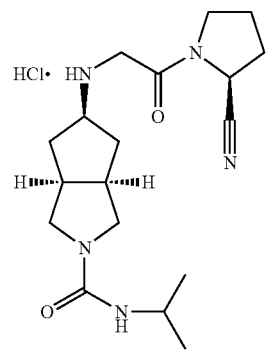

7
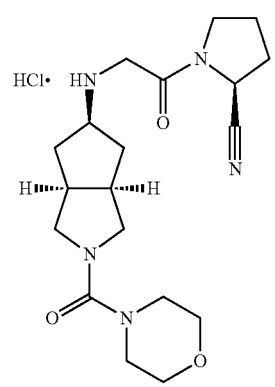

-continued

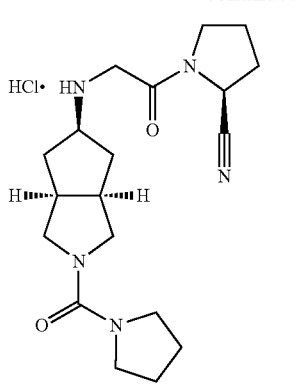

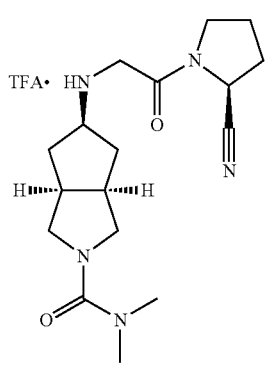

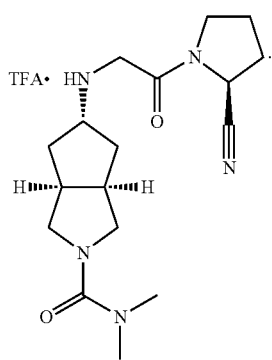

7. A pharmaceutical composition comprising a therapeutically acceptable amount of at least one compound of any one of claims 1-6, and a pharmaceutically acceptable carrier.

8. A process for the preparation process of a compound of formula (IB) of claim 2, comprising the following steps of:

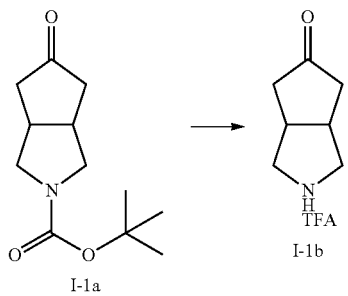

reacting starting material 5-oxo-hexahydro-cyclopenta[c]pyrrole-2-carboxylic acid tert-butyl ester (I-1 a) with trifluoroacetic acid in a solvent of dichlormethane in an ice-water bath to obtain hexahydro-cyclopenta[c]pyrrol-5-one triflutate (I-1b);

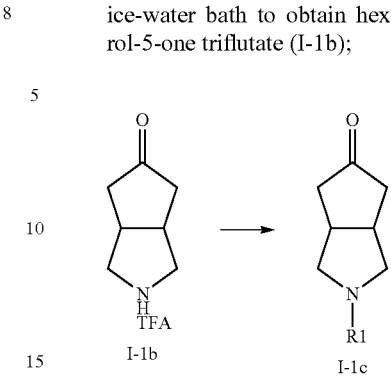

reacting hexahydro-cyclopenta[c]pyrrol-5-one triflutate (I-1b) with an acyl chloride or ester in the presence of base to obtain a compound of formula (I-1c);

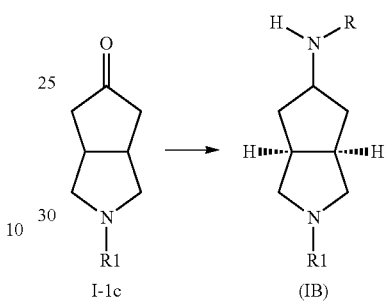

reacting the compound of formula (I-1c) with an equivalent amount of an amine, sodium triacetoxyborohydride and triethylamine in a solvent comprising methanol at room temperature to obtain the compounds of formula (IB);
wherein:
R is the following formula:

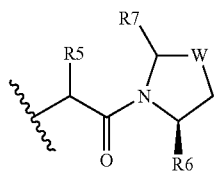

$R_1$ is a member selected from the group consisting of hydrogen, alkyl, cycloalkyl, heterocyclo alkyl, aryl, heteroaryl, —C(O)NR$_3$R$_4$, —C(O)R$_3$ and —C(O)O R$_3$, wherein the alkyl, cycloalkyl, heterocyclo alkyl, aryl or heteroaryl may be substituted with one or more groups selected from the group consisting of alkyl, aryl, hydroxyl, amino, alkoxyl, aryloxyl and heterocyclo alkyl;

$R_3$ and $R_4$ are each independently a member selected from the group consisting of hydrogen, alkyl, cycloalkyl, aryl, heteroaryl and heterocyclo alkyl, wherein the alkyl, cycloalkyl, aryl, heteroaryl or heterocyclo alkyl may be substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, cyano, hydroxyalkyl, heterocyclo alkyl, heterocyclo alkoxyl, trifluoromethyl, carboxylic acid and carboxylic ester; and $R_3$ and $R_4$ are attached together with the N atom to form a 3 to 8 membered hetero ring, wherein the 3 to 8 membered hetero ring may contain one or more heteroatoms selected from the group consisting of N, O and S atom, and the 3 to 8 membered rings may be substituted with one or more groups selected from the group consisting of alkyl, aryl, heteroaryl, haloalkyl, haloalkoxyl, hydroxyl, amino, cyano, alkoxyl, aryloxyl, hydroxyalkyl, heterocyclo alkyl, carboxylic acid, carboxylic ester, halogen and —$NR_3R_4$;

$R_5$ is a member selected from the group consisting of hydrogen, alkyl, cycloalkyl, aryl, heteroaryl and heterocyclo alkyl, wherein the alkyl, cycloalkyl, aryl, heteroaryl or heterocyclo alkyl may be substituted with one or more groups selected from the group consisting of alkyl, cycloalkyl, aryl, heteroaryl, alkoxyl, cycloalkoxyl, aryloxyl, heteroaryloxyl, halogen, hydroxyl, amino, alkylamino, cyano, hydroxyalkyl, heterocyclo alkyl, heterocyclo alkoxyl, carboxylic acid and carboxylic ester;

$R_6$ and $R_7$ are each independently a member selected from the group consisting of alkyl, aryl, heteroaryl, haloalkyl, haloalkoxyl, hydroxyl, amino, cyano, alkynyl, alkoxyl, aryloxyl, hydroxyalkyl, heterocycle alkyl, carboxylic acid, carboxylic ester and halogen; and W is C.

9. A method of treating non-insulin-dependent diabetes mellitus which comprises administering to a patient in need thereof a therapeutically effective amount of a dipeptidyl peptidase inhibitor according to claim 1.

10. A method of treating non-insulin-dependent diabetes mellitus which comprises administering to a patient in need thereof a therapeutically effective amount of a dipeptidyl peptidase inhibitor according to claim 6.

\* \* \* \* \*